(12) United States Patent
Brenneman et al.

(10) Patent No.: US 8,641,747 B2
(45) Date of Patent: Feb. 4, 2014

(54) DEVICES FOR ARTERIO-VENOUS FISTULA CREATION

(75) Inventors: Rodney Brenneman, San Juan Capistrano, CA (US); Douglas S. Cali, Mission Viejo, CA (US); J. Christopher Flaherty, Topsfield, MA (US)

(73) Assignee: Rox Medical, Inc., San Clemente, CA (US)

( * ) Notice: Subject to any disclaimer, the term of this patent is extended or adjusted under 35 U.S.C. 154(b) by 1813 days.

(21) Appl. No.: 11/152,621

(22) Filed: Jun. 13, 2005

(65) Prior Publication Data

US 2005/0277965 A1 Dec. 15, 2005

Related U.S. Application Data

(60) Provisional application No. 60/579,913, filed on Jun. 14, 2004.

(51) Int. Cl.
*A61F 2/06* (2013.01)
(52) U.S. Cl.
USPC ........................................ 623/1.11
(58) Field of Classification Search
USPC ......... 606/139, 142, 151, 153–156; 623/1.11, 623/1.13–1.15, 1.23
See application file for complete search history.

(56) References Cited

U.S. PATENT DOCUMENTS

| | | | |
|---|---|---|---|
| 3,882,862 A | 5/1975 | Berend | |
| 4,762,128 A * | 8/1988 | Rosenbluth | 606/192 |
| 5,108,420 A | 4/1992 | Marks | |
| 5,682,906 A | 11/1997 | Sterman et al. | |
| 5,690,670 A * | 11/1997 | Davidson | 606/198 |
| 5,718,725 A | 2/1998 | Sterman et al. | |
| 5,807,258 A * | 9/1998 | Cimochowski et al. | 600/454 |
| 5,830,222 A | 11/1998 | Makower | |
| 5,830,224 A | 11/1998 | Cohn et al. | |
| 5,836,913 A | 11/1998 | Orth et al. | |
| 6,099,542 A | 8/2000 | Cohn et al. | |
| 6,120,522 A * | 9/2000 | Vrba et al. | 606/190 |
| 6,190,353 B1 * | 2/2001 | Makower et al. | 604/95.01 |
| 6,248,117 B1 | 6/2001 | Blatter | |
| 6,254,631 B1 * | 7/2001 | Thompson | 623/1.15 |
| 6,361,545 B1 | 3/2002 | Macoviak et al. | |

(Continued)

FOREIGN PATENT DOCUMENTS

| | | |
|---|---|---|
| JP | 2003-505182 A | 2/2003 |
| JP | 2004-501720 A | 1/2004 |
| WO | WO 2004/091696 | 10/2004 |

OTHER PUBLICATIONS

International search report and written opinion dated May 11, 2006 for PCT/US2005/020360.

*Primary Examiner* — Gregory Anderson
(74) *Attorney, Agent, or Firm* — Wilson, Sonsini, Goodrich & Rosati

(57) ABSTRACT

Devices are disclosed for the formation of arterio-venous fistula creation. Embodiments include a femoral access approach to the creation of an Aorta-caval fistula at the bifurcation of the Aorta and the Inferior Vena Cava; an apparatus for the creation, modification and maintenance of a fistula; and a method of supplying oxygenated blood to the venous circulation of a patient. The devices, systems and methods can be used to treat patients with one or more numerous ailments including chronic obstructive pulmonary disease, congestive heart failure, hypertension, hypotension, respiratory failure, pulmonary arterial hypertension, lung fibrosis and adult respiratory distress syndrome.

79 Claims, 13 Drawing Sheets

(56) References Cited

U.S. PATENT DOCUMENTS

| | | |
|---|---|---|
| 6,451,048 B1 | 9/2002 | Berg et al. |
| 6,464,665 B1 | 10/2002 | Heuser |
| 6,579,311 B1 | 6/2003 | Makower |
| 6,669,709 B1 | 12/2003 | Cohn et al. |
| 6,695,878 B2 | 2/2004 | McGuckin, Jr. et al. |
| 6,736,825 B2 | 5/2004 | Blatter et al. |
| 6,746,426 B1 | 6/2004 | Flaherty et al. |
| 6,746,464 B1 | 6/2004 | Makower |
| 6,926,690 B2 | 8/2005 | Renati |
| 7,011,094 B2 | 3/2006 | Rapacki et al. |
| 7,056,326 B2 | 6/2006 | Bolduc et al. |
| 7,083,631 B2 * | 8/2006 | Houser et al. .................. 606/153 |
| 2002/0169377 A1 | 11/2002 | Khairkhahan et al. |
| 2004/0087984 A1 | 5/2004 | Kupiecki et al. |
| 2004/0249335 A1 | 12/2004 | Faul et al. |
| 2005/0107733 A1 | 5/2005 | Faul et al. |
| 2005/0277964 A1 | 12/2005 | Brenneman et al. |
| 2005/0277967 A1 | 12/2005 | Brenneman et al. |
| 2006/0184011 A1 | 8/2006 | Macaulay et al. |

* cited by examiner

Fig. 6
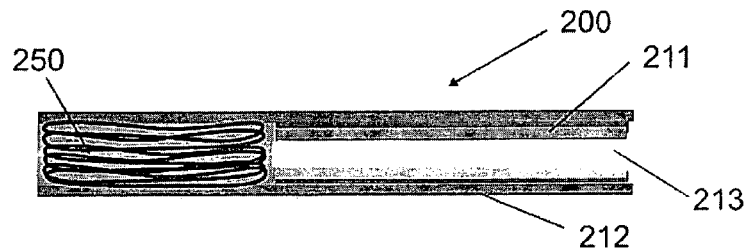
Fig. 7
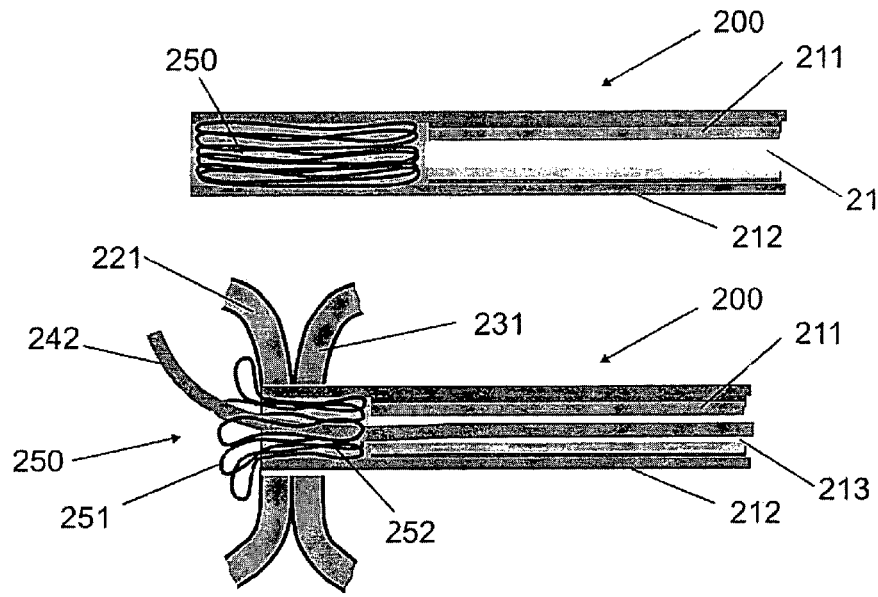
Fig. 8
Fig. 9
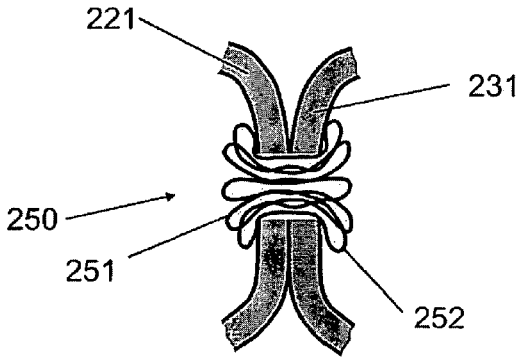

DEVICES FOR ARTERIO-VENOUS FISTULA CREATION

CROSS-REFERENCES TO RELATED APPLICATIONS

This application claims the benefit of prior provisional application Ser. No. 60/579,913, filed on Jun. 14, 2004, the full disclosure of which is incorporated herein by reference.

BACKGROUND OF THE INVENTION

Field of the Invention

The present invention relates generally to medical devices and methods. More particularly, the present invention relates to devices and methods for creating a flow of oxygenated blood into the venous system of a patient.

Chronic obstructive pulmonary disease affects millions of patients in the United States alone. The present standard of care is oxygen therapy, which requires a patient to remain near a stationary oxygen source or carry a bulky oxygen source when away from home or a treatment facility. It is easy to appreciate that such oxygen therapy has many disadvantages.

Lung reduction surgery has recently been proposed for treating patients with chronic pulmonary disease. Such surgery, however, is not a panacea. It can be used on only a small percentage of the total patient population, requires long recovery times, and does not always provide a clear patient benefit. Even when successful, patients often continue to require supplemental oxygen therapy.

There is therefore a need for improved approaches, including both devices and methods, for treating patients suffering from chronic obstructive pulmonary disease. If would be desirable if such devices and methods were also useful for treating patients with other conditions, such as congestive heart failure, hypertension, lung fibrosis, adult respiratory distress syndrome, and the like. Such devices and methods should provide for effective therapy, preferably eliminating the need for supplemental oxygen therapy in the treatment of chronic obstructive pulmonary disease. After the procedures, such devices and methods should optionally be adjustable so that the degree of therapy is responsive to the patient's needs at any particular time. At lease some of these objectives will be met by the invention described hereinafter.

BRIEF SUMMARY OF THE INVENTION

The apparatus of the present invention are useful for creating an aorto-caval fistula in a patient. The fistula is made at or near the bifurcation of the Aorta and the Inferior Vena Cava (IVC) between a starting vessel and a target vessel. An arterial catheter is placed in the Aorta superior to the aortic bifurcation, and a venous catheter is placed in the Vena Cava, inferior to the fistula creation site. A crossing needle device is introduced into the starting vessel, and contrast medium is injected through a catheter in the target vessel. A crossing needle of the crossing needle device is advanced from the starting vessel to the target vessel, and a guidewire is passed through the crossing needle into the target vessel. An anastomotic clip delivery device is advanced over the guidewire, and an anastomotic clip is deployed between the starting vessel and the target vessel, after which the anastomotic clip delivery device is removed.

In one aspect of the present invention, an apparatus for delivering a vessel to vessel anastomotic clip in a patient is disclosed. The apparatus comprises an elongate core which includes a lumen extending from a proximal end to a distal end. The core includes a reduced diameter segment near its distal end. An outer sheath slidingly receives the core, and an anastomotic clip is maintained between the core and the outer sheath at the reduced diameter segment. A handle is located on the proximal end of the apparatus, such that manipulation of the handle by an operator will deploy the anastomotic clip and a connection between an artery and a vein can be maintained over a period of time.

In another embodiment of the apparatus of the present invention, the core includes a dilating tip. In another embodiment, the core includes radiopaque markers, such as to identify the location of the reduced diameter segment. In one preferred embodiment, the anastomotic clip is self expanding. In an alternative embodiment, the clip is plastically deformable, such as to be expanded by a balloon. In another alternative embodiment, the anastomotic clip includes self expanding portions and plastically deformable portions. In another embodiment the anastomotic clip includes a covering along at least a part of its length. In another preferred embodiment the anastomotic clip includes two pieces, such as could be implanted in a single or multiple deployment steps. In a preferred embodiment, the anastomotic clip is deployed by pushing the core forward. In an alternative embodiment, the clip is deployed by pulling the sheath back. In yet another alternative embodiment, the clip is deployed by a combination of pulling the sheath back and pushing the core forward.

In yet another embodiment of the apparatus of the present invention, the anastomotic clip includes a flow control element which can adjust the flow through the anastomotic clip. In an alternative or additional embodiment, the anastomotic clip includes an integrated sensor, such as could supply flow control information.

In yet another embodiment of the apparatus of the present invention, the apparatus further comprises a vessel crossing needle element with a slidingly advanceable needle with a lumen therethrough. In a preferred embodiment the apparatus includes a needle injection mechanism. In another preferred embodiment the vessel crossing needle element can be removed from the apparatus. In another preferred embodiment the crossing needle is elastically biased to be in a retracted position. In another preferred embodiment, the crossing needle is curved, such as a radius of curvature less than thirty degrees. In another preferred embodiment, the vessel crossing needle element comprises an integrated visualization element, such as an ultrasound imaging device.

In yet another embodiment of the apparatus of the present invention, the apparatus further comprises a fistula enlarging element. In a preferred embodiment the fistula enlarging element is a balloon. In another preferred embodiment the fistula enlarging element is a debulking device such as a radiofrequency ablating device or a tissue cutting element.

In yet another embodiment of the apparatus of the present invention, the apparatus further comprises a fistula maintenance device. In a preferred embodiment the fistula maintenance device includes one or more of: a balloon, a debulking device, a radiation source, an implant placement device, an implant removal device, a heating or cooling element, a light emitting element and a drug delivery element.

In yet another embodiment of the apparatus of the present invention, the apparatus further comprises visualization markers. In a preferred embodiment, the visualization markers indicate rotational orientation of the apparatus. In another preferred embodiment the visualization markers are integrated into one or more of: the core, the outer sheath, a needle deployment catheter and a balloon catheter.

In yet another embodiment of the apparatus of the present invention, the apparatus further comprises a visualization device. In a preferred embodiment the visualization device is an ultrasound device. In a preferred embodiment, the visualization device is removable. In an alternative preferred embodiment, the visualization device is integrated into the apparatus of the present invention.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 6 is a cross sectional view of an anastomotic clip deployment device consistent with the present invention;

FIG. 7 is a cross sectional view of an anastomotic clip deployment device shown at a fistula creation site prior to full deployment of an anastomotic clip;

FIG. 8 is a cross sectional view of an anastomotic clip deployment device shown at a fistula creation site prior to full deployment of an anastomotic clip;

FIG. 9 is a cross sectional view of a fistula creation site with an anastomotic clip deployed;

DETAILED DESCRIPTION OF THE INVENTION

Reference will now be made in detail to the present embodiments of the invention, examples of which are illustrated in the accompanying drawings. Wherever possible, the same reference numbers will be used throughout the drawings to refer to the same or like parts.

Figure 1:
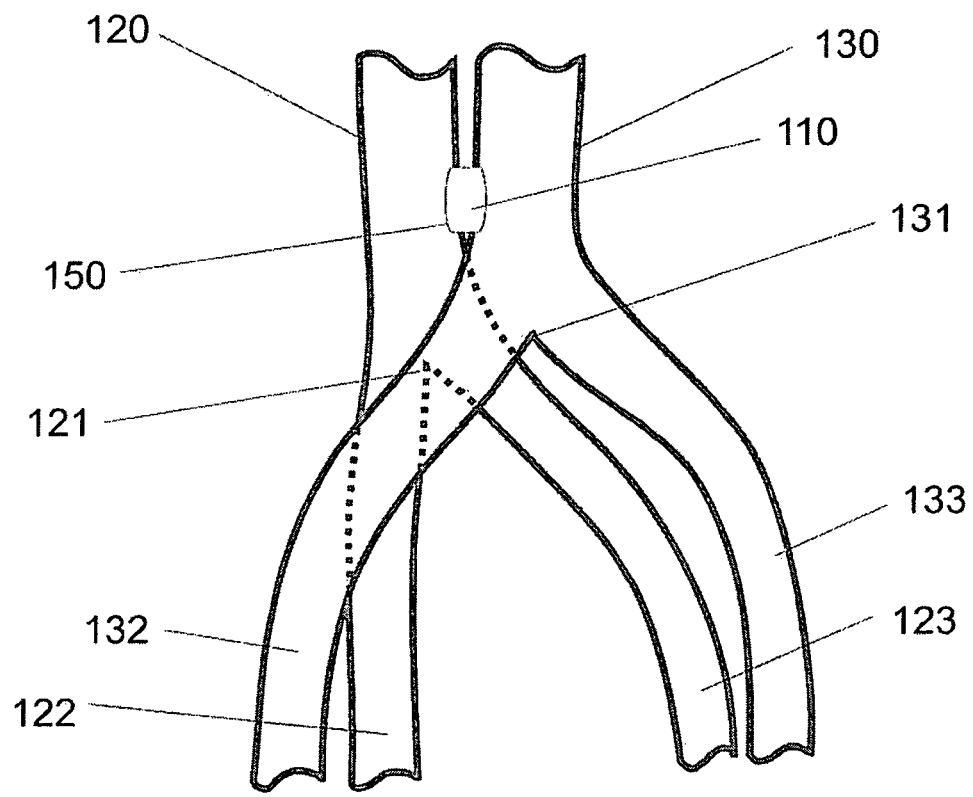
FIG. 1 illustrates a fistula consistent with the present invention.

FIG. 1 depicts a distal aorto-caval fistula, fistula 110, created in a patient, such as a human or other animal, near the bifurcation of the Aorta 130 and the Inferior Vena Cava, IVC 120. Fistula 110 is located proximate to Aortic bifurcation 131 and IVC bifurcation 121 and provides oxygenated blood from the higher pressure arterial system to the venous system such that blood flows from the Aorta 130 to the IVC 120 through shunt device 150 and fistula 110. This distal aorto-caval fistula 110, is maintained in a fluidly open state by way of a vessel anastomosis clip, shunt device 150. Shunt device 150 is manufactured from one or more biocompatible materials and can provide numerous functions. Shunt device 150 can provide tension between Aorta 130 and IVC 120 at the fistula site to create a temporary or long term fluid seal between the tissue surrounding the openings in each vessel wall. Shunt device 150 can provide sufficient radial force, either temporary or long term, to maintain a lumen between Aorta 130 and IVC 120. Shunt device 150 can act as a depot for one or more pharmaceutical or other agents such as to enhance long term patency and biocompatibility. Also, shunt device 150 can provide a control means to adjust the flow of blood from the arterial system to the venous system, either automatically or in combination with a separate device. Shunt 150 can provide other functions such as to enhance the resultant therapeutic benefit of fistula 110 and/or prevent or reduce undesired side effects such as thrombus or atheroma formation, neointimal proliferation, vessel erosion and other adverse conditions.

Shunt device 150 has been placed in a surgical or interventional procedure, or a combination of the two. In an open surgical procedure, a clinician use scalpels and other cutting means to expose the associated vessels to create fistula 110. Alternative, minimally invasive surgical procedures make use of one or more tubes, placed through small incisions in the skin, through which the clinician can pass various visualization and surgical tools to create the connection between the Aorta 130 and IVC 120. In an interventional procedure, similar to balloon angioplasty and interventional atherectomy procedures, catheter devices are placed through introducer tools into one or more vessels, and advanced through the vasculature to a specific location by guided fluoroscopy or ultrasound. Access to fistula 110 can be made superior to fistula 110 such as by way of jugular veins and arteries. In a preferred embodiment, interventional access is provided from the groin area of the patient, such as by way of Right Arterial Iliac 132 or Left Arterial Iliac 133 for access to the Aorta 130, and Right Venous Iliac 122 or Left Venous Iliac 123 for access to IVC 120.

The flow of oxygenated blood from the arterial system through fistula 110 to the venous system can provide therapeutic benefit to patients suffering from one or more diseases including but not limited to: chronic obstructive pulmonary disease, congestive heart failure, hypertension, hypotension, respiratory failure, pulmonary arterial hypertension, lung fibrosis and adult respiratory distress syndrome. The therapeutic benefit results from one or more factors as is described herebelow.

Blood returning to the right side of the heart is pumped to the lungs where is becomes oxygenated or re-oxygenated before returning to the left side of the heart to be pumped to the body's tissues via the arterial system. Blood flow experiences a resistance from all of the system vasculature, which is referred to as systemic vascular resistance (SVR). The recirculated blood that passes through shunt device 150 bypasses the peripheral microcirculation and decreases the SVR. To achieve therapeutic benefit, a decrease of SVR of at least 5% would be desired.

Blood flows through shunt device 150 from Aorta 130 to IVC 120 because of the pressure gradient between the blood in the arterial system and the blood in the venous system. In a preferred embodiment, the flow through shunt device 150 is at least 5 ml/min. It may be desirable for shunt device 150 to self-regulate flow, or be controllable via internal or external means, as will be described in reference to subsequent figures herebelow. The flow of arterial blood into IVC 120 has cardiac, circulatory and respiratory effects. Cardiac output increases with a decrease in SVR due to the increased pressure gradient. This increase in cardiac output could benefit patients with cardiac failure or patients who suffer from low cardiac output, such as congestive heart failure patients.

Regarding respiratory effects, the oxygenated blood that mixes with the venous blood already present in IVC 120 results in a higher $O_2$ concentration venous blood entering the right atrium of the heart. This high $O_2$ concentration venous blood leads to an increase in the $O_2$ concentration in arterial blood in two ways: (1) since the blood that is shunted does not have $O_2$ extracted by tissue capillaries, the blood returning to the lungs has a higher $O_2$ concentration after the creation of the shunt than before, and (2) the binding of $O_2$ to the hemoglobin component of blood is more efficient with a higher Pa $O_2$ (partial pressure of $O_2$ in arterial plasma) resulting in increased oxygen carrying capacity. These advantageous respiratory effects could benefit patients with pulmonary arterial hypertension by lowering pulmonary arterial blood pressure, patients with heart or respiratory failure by increasing arterial oxygen concentration, or patients with chronic obstructive pulmonary disease by increasing blood oxygen concentration.

Regarding circulatory effects, another important benefit of decreasing SVR is related to the fact that the lungs regulate their blood flow according to the $O_2$ content. An increase in the $O_2$ content should decrease the pulmonary arterial blood pressure. These advantageous circulatory effects could benefit patients with hypertension by lowering systemic arterial, systolic and/or diastolic blood pressure. These cardiac, respiratory and circulatory effects could also benefit numerous other patients with circulatory or other diseases including but not limited to: hypotension (by increasing cardiac output), lung fibrosis, adult respiratory distress syndrome, and the like.

Various interventional techniques can be used to create a fistula at or near the bifurcation of the Aorta and the Inferior Vena Cava as was depicted in reference to FIG. 1. In a preferred method, a fistula is created between a starting vessel and a target vessel, wherein the starting vessel and target vessel consist of an artery and a vein or a vein and an artery, respectively. An arterial catheter is placed in the Aorta superior to the aortic bifurcation, and a venous catheter is placed in the Vena Cava, inferior to the fistula creation site. A crossing needle device that incorporates a hollow needle, advanceable with controls at the device's proximal end, is placed in the starting vessel, either an artery or a vein. Radiographic dye, or other contrast medium is injected through the catheter in the target vessel. The crossing needle of the crossing needle device is advanced, the needle penetrating first the wall of the starting vessel and then the wall of the target vessel, eventually with the tip of the residing within the lumen of the target vessel. A guidewire is passed through the crossing needle down the lumen of the target vessel. An anastomotic clip delivery system is advanced over the previously placed guidewire, and used to place an anastomotic clip between the starting vessel and the target vessel.

Figure 2:
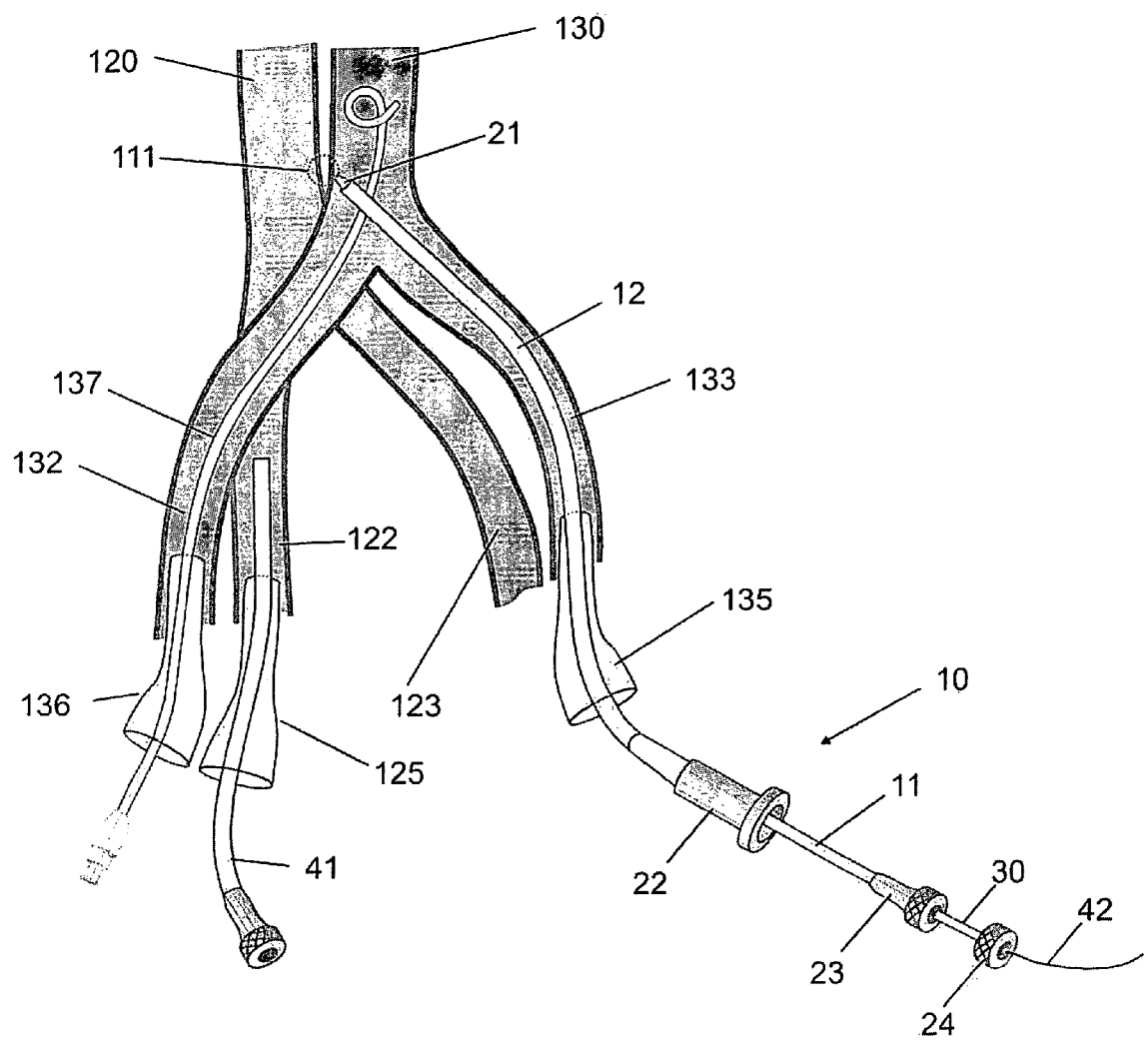
FIG. 2 illustrates fistula creation apparatus consistent with the present invention.

Referring to FIGS. 2 through 9, a method of creating an aorto-caval fistula is described. Depicted in FIG. 2 is Aorta 130, which bifurcates into Right Arterial Iliac 132 and Left Arterial Iliac 133. Also depicted is IVC 120 which bifurcates into Right Venous Iliac 122 and Left Venous Iliac 123. An introducer sheath, venous introducer 125 is placed in the groin area of the patient, into a right femoral vein to provide access to Right Venous Iliac 122. A venous catheter, imaging catheter 41, used for injecting contrast medium and other agents, as well as the passage of guidewires and other devices through an inner lumen, is placed through venous introducer 125 so that its tip resides inferior to the intended location for the fistula, fistula site 111. This tip location allows radiographic dye or other contrast medium injected through imaging catheter 41 to travel, with the venous blood flow, past fistula site 111 and toward the heart of the patient.

A second introducer sheath, arterial introducer 135 is placed in the groin area of the patient into the left femoral artery. Fistula creation apparatus 10, is inserted through arterial introducer 135 and advanced to a location proximate fistula creation site 111. Apparatus 10 can provide numerous functions including but not limited to: injection of contrast medium including radiographic dyes and ultrasonic medium, injection of drugs or other agents, aspiration of blood, vessel to vessel needle advancement, visualization of internal structures such as via ultrasound, fistula and/or implant dilation, fistula and/or implant contraction, tissue debulking, placement of an anastomotic clip, removal of an anastomotic clip, passage of guidewires and other small diameter devices, placement of a fistula treatment device, placement of a anastomotic clip treatment device, placement of a flow modification device, placement of a visualization device such as an intravascular ultrasound catheter and other functions. These various functions can be performed by or with the assistance of apparatus 10 through the use of functional elements integrated into apparatus 10, or separate devices which can be passed through one or more lumens accessible from the proximal end of apparatus 10.

Located at the proximal end of apparatus 10 are various knobs which are used to rotate, advance, retract, manipulate, activate, or otherwise control the slidable tubes, needles and other elements of apparatus 10. Sheath advancement knob 22 is mechanically connected to outer sheath 12 which surrounds various internal tubes, elements and lumens. In a preferred embodiment, apparatus 10 includes a visualization element, such as an ultrasound element, not shown. The visualization element can produce, through electronic or other means, a visual representation of the device and neighboring tissue. The visualization element may be an ultrasound catheter, such as a rotational or fixed array ultrasound catheter, which creates a cross-sectional image of the area surrounding the device. The ultrasound catheter can be inserted into a lumen of apparatus 10, or may be an integrated ultrasound device that has as an array of ultrasound crystals which are fixedly mounted along the distal portion of apparatus 10 and contain electronic connections that are connected to a proximal handle of apparatus 10, these connections mating with a standard ultrasonic viewing monitor. In an alternative or additional, preferred embodiment, apparatus 10 includes one or more visualization markers, such as radiographic markers or embedded agents such as barium sulfate, or ultrasonically visible markers, all not shown. These markers can be used to perform controlled advancements, retractions, rotations and other positioning of apparatus 10 during the fistula creation procedures An internal tube, core 11 is slidingly received within outer sheath 12, and has at its distal end tip 21, which preferably has a dilating tip shape, and is atraumatic. Tip 21 is advanced to fistula site 111, by advancing apparatus 10 through arterial introducer 135. Within core 11 is another tubular device, a flexible, advanceable needle, needle 30 which has attached at its proximal end, needle advancement knob 24. Slidingly received within needle 30 is a standard interventional guidewire, guidewire 42. Needle 30 may consist of an outer protective sheath, not shown, with a flexible, advanceable needle contained within its lumen.

Tip 21 is positioned against the wall of Aorta 130 such that needle 30 can be advanced from an artery, Aorta 130, to a vein, IVC 120. In an alternative, preferred embodiment, the procedure is performed from vein to artery, such as from IVC 120 to Aorta 130. Prior to advancing needle 30 out of tip 21, radiographic dye can be injected to visualize the border of the starting vessel, Aorta 140, under fluoroscopy. An injection of contrast medium from a catheter in the target vessel can visualize the border of the target vessel walls as well. Contrast medium can be injected through the lumen in needle 30, or via a separate lumen incorporated through the length of apparatus 10.

Referring specifically to FIG. 2, another introducer sheath, arterial introducer 136 is placed in the groin area of the patient and into the right femoral artery. Pigtail catheter 137 is inserted through arterial introducer 136 and advanced to a location superior to fistula creation site 111. Contrast medium injections can be performed through pigtail catheter 137, shown only in FIG. 2 but applicable to FIGS. 3 through 10, such that arterial flow can be visualized under fluoroscopy prior to, during and after fistula creation for anatomical landmarking including but not limited to: location of vessel walls, sizing of vessel and fistula lumens, estimation of blood flow and other angiographic purposes.

In the artery to vein approach depicted in FIG. 2, the outer sheath 12 can be positioned against the medial aortic wall to provide support as needle 30 is advanced. Typical advancement distance of needle 30 is at least 5 mm, which can be controlled with markings or other control means located on the proximal end of apparatus 10, not shown. After the needle 30 is advanced, or partially advanced, a contrast medium injection can be performed through the lumen in needle 30, to confirm access of the target vessel, IVC 120.

Figure 3:
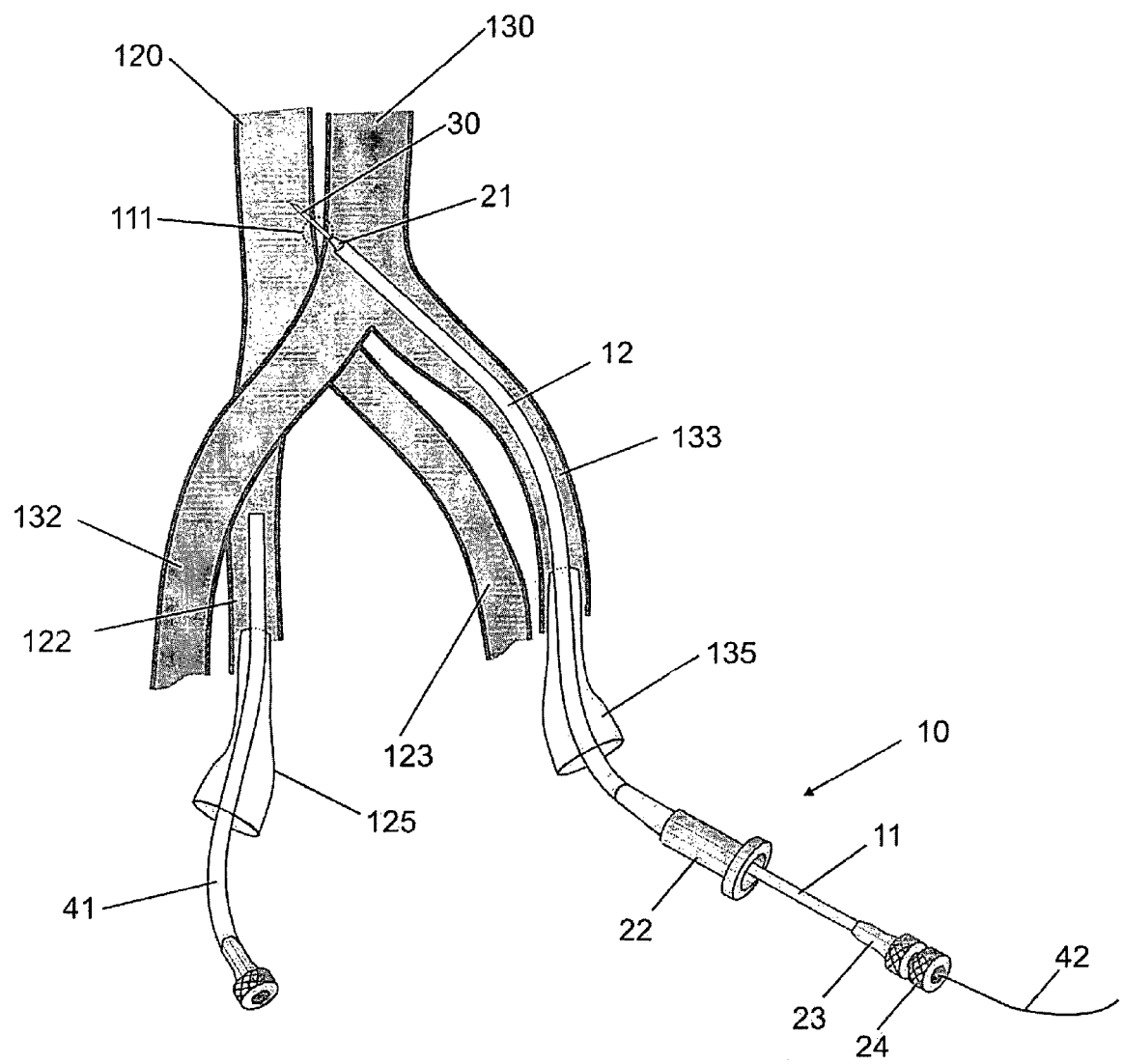
FIG. 3 illustrates fistula creation apparatus consistent with the present invention.

Referring now to FIG. 3, needle 30 has been advanced from Aorta 130 into IVC 120 by advancing needle advancement knob 24. Advancement can be rapid, such as via a needle injection mechanism incorporated into a proximal handle of apparatus 10, injection mechanism not shown, and the injection can be performed in a single continuous advancement or in multiple discrete steps. In the discrete step approach, access of the target vessel can be confirmed by repeat attempts at advancing or probing of guidewire 42, and/or by injection of contrast medium through the lumen of needle 30 and/or by aspiration of blood through needle 30. Visual examination of blood color can indicate arterial or venous blood withdrawn to confirm access to artery or vein respectively. When properly accessed, the distal portion of guidewire 42 can be advanced from Aorta 130 into IVC 120 or into the Right Iliac Vein 132.

Figure 4:
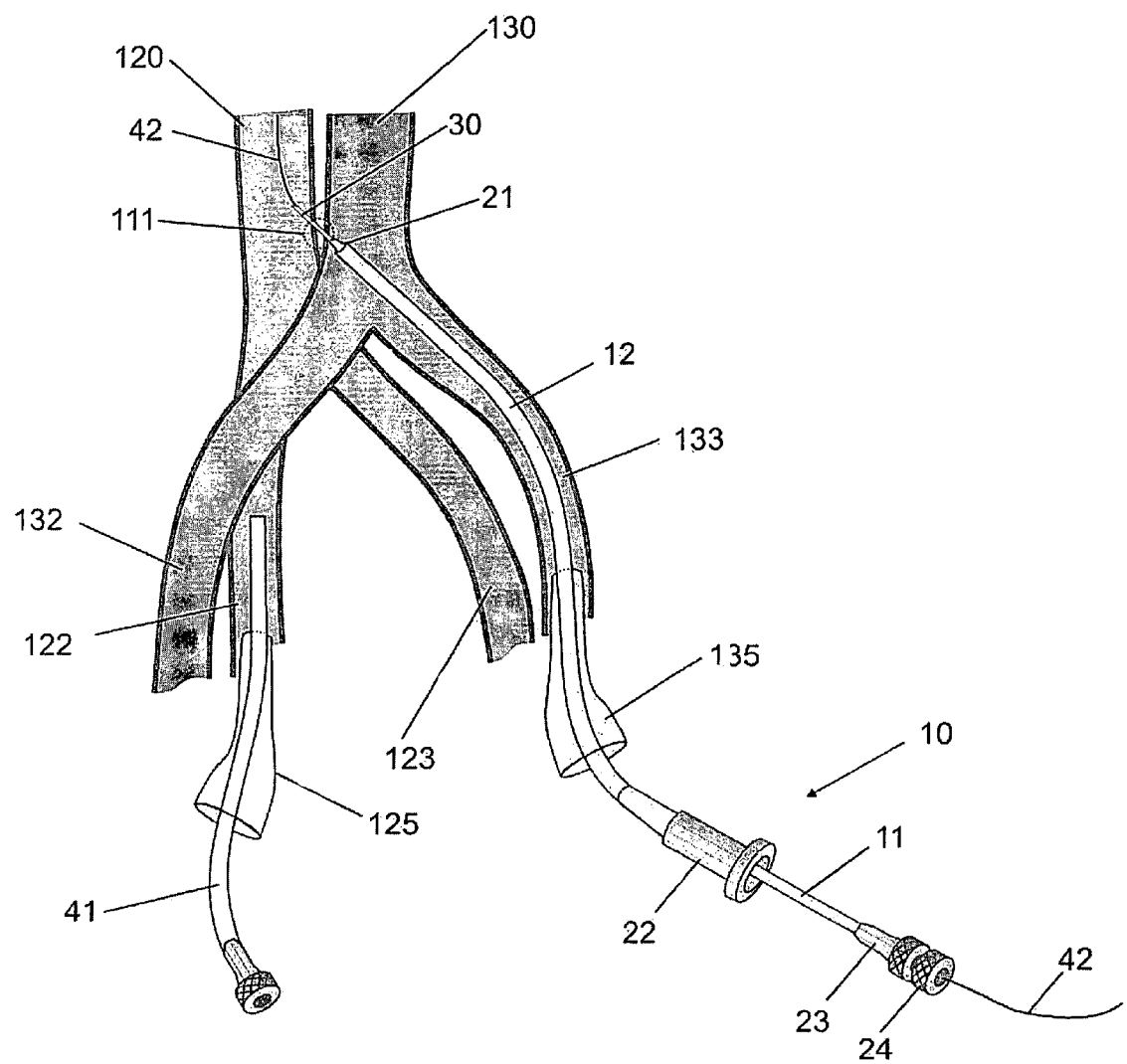
FIG. 4 illustrates fistula creation apparatus consistent with the present invention.

Referring now to FIG. 4, guidewire 42 has been advanced in a superior direction into IVC 120. Needle 30 is ready to be retracted, and depending on the configuration of apparatus 10, either removed entirely from a lumen of apparatus 10 or retracted to a less distal location but remaining within apparatus 10. In a preferred embodiment, an automatic retraction mechanism, such as a spring loaded mechanism, not shown, is integral to apparatus 10. In various preferred embodiments of the present invention, outer sheath 12 and its internal components are removed, and a second catheter device of apparatus 10 is inserted over guidewire 42 to place an anastomotic clip. In alternative preferred embodiments of the present invention, outer sheath may be removed or partially removed, to load an anastomotic clip delivery device. In another preferred embodiment, apparatus 10 and outer sheath 12 remain at the location proximate fistula site 111, and an anastomotic clip delivery device is available, either by being already in place, or loaded within a lumen of outer sheath 12. In a preferred embodiment, an anastomotic clip delivery device is inserted after needle 30 is removed from the lumen of outer sheath 12.

Figure 5:
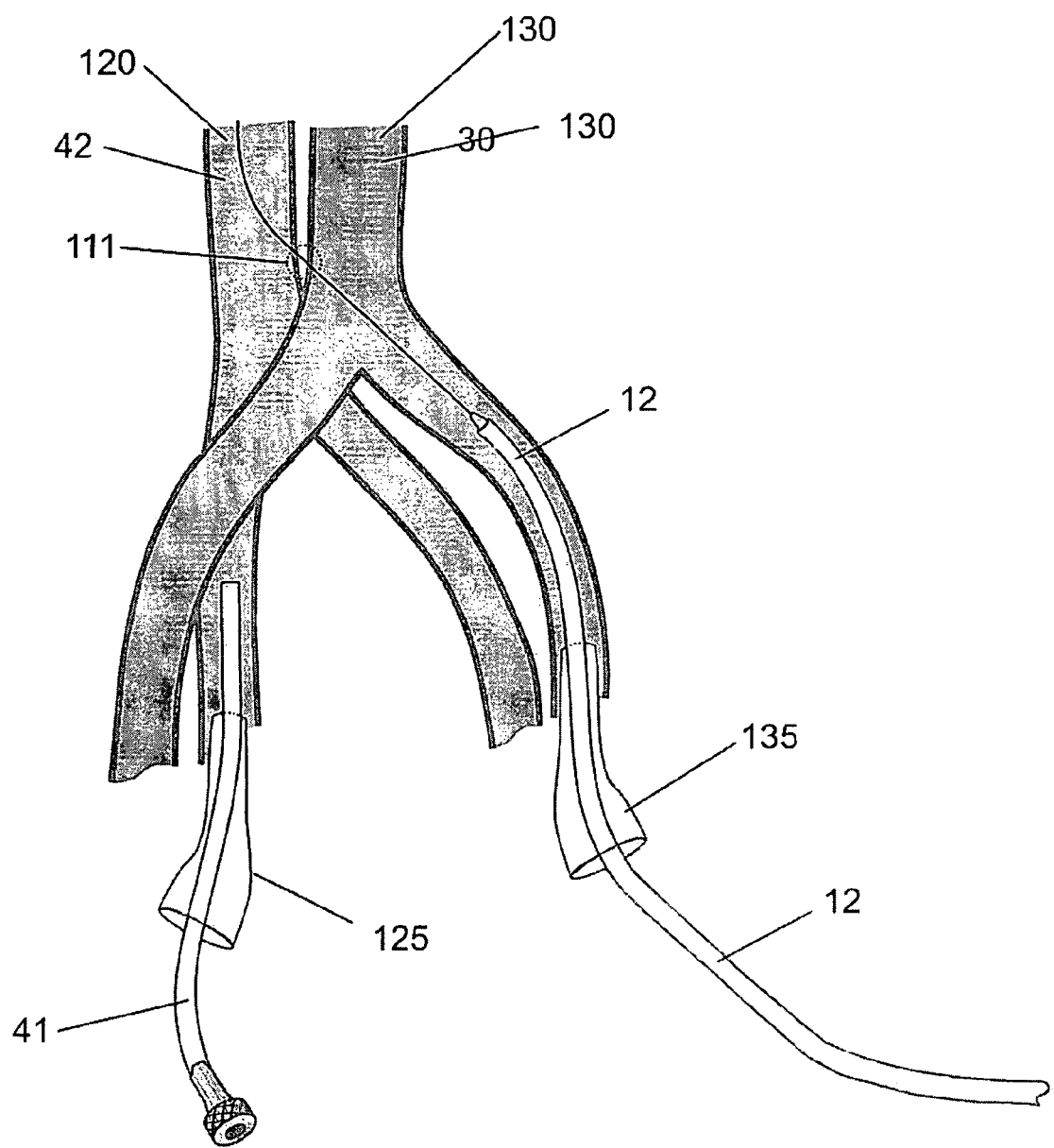
FIG. 5 illustrates fistula creation apparatus consistent with the present invention.

FIG. 5 depicts outer sheath 12 in a partially retracted position, the retraction being performed while maintaining and/or advancing guidewire 24 such that a sufficient portion of guidewire 24 remains within IVC 120. Prior to the placement of the anastomotic clip, the tissue between the lumens of the Aorta 130 and IVC 120, such as the vessel wall tissues and tissue external to the walls, may need to be expanded or dilated with one or more devices such as a standard angioplasty balloon. Alternatively or additionally, it may be desirous to remove a portion of this tissue utilizing one or more debulking tools such as ablative tools or tissue cutting and removing tools. These various methods of enlarging the opening, or flow path, between the two vessels can be performed over needle 30 or over a needle assembly, not shown, or over the guidewire 42 after needle 30 or a needle assembly is retracted.

Apparatus 10 may include various flow path or channel creation means, described in more detail in reference to subsequent figures. Flow path dilation elements may include the incorporation of a compliant or non-compliant balloon, with an inflation lumen and port located on the proximal end of apparatus 10, all not shown. The balloon may be integrated into a distal portion of the needle assembly, on a distal portion of outer sheath 12, on a distal portion of core 11, or on a separate tubular device advanceable through a lumen of apparatus 10, all not shown. Debulking means may include one or more of an energy ablation device, such as a radiofrequency ablation element, either monopolar or bipolar, or a cutting element similar to a pull back cutting element used in pull back atherectomy procedures. The debulking means can be advanced from the starting vessel to the target vessel to perform the debulking procedure, advanced to the target vessel first and then pulled back from the target vessel to the starting vessel to perform the debulking procedure, or both. In all flow path creation and enlargement procedures, the flow path creation and enlargement elements can be integrated into one or more components of apparatus 10 or be included in a separate tubular structure advanceable through a lumen of apparatus 10. These flow path creation and enlargement procedures are all performed over the guidewire placed from the starting vessel to the target vessel.

FIG. 6 depicts apparatus 200, an anastomotic clip deployment apparatus consistent with the present invention. Apparatus 200 is a flexible, catheter device, which includes a sliding core, core 211, which has a lumen, lumen 213, from its proximal end, not shown, to its distal end, to allow placement over a guidewire. Apparatus 200 includes outer sheath 212, which surrounds and slidingly receives core 211. Located at or near the distal end of apparatus 200, is a preloaded anastomotic clip, clip 250, which is a self-expanding device constrained by outer sheath 212 which can be deployed to secure and create a fistula between an artery and a vein, such as the Aorta and the IVC. Clip 250 can be deployed by advancing core 211 forward while maintaining outer sheath 212 in a relatively fixed position, by retracting sheath 212 while maintaining core 211 in a relatively fixed position, or by both advancing core 211 and retracting outer sheath 212. A deployment trigger and trigger mechanism, not shown, may be incorporated into apparatus 200 such that the retraction and/or advancement steps, are accomplished by activating the trigger, such that timing, relative timing and advancement and retraction distances are predetermined by the trigger mechanism. In a preferred embodiment, some amount of advancement and retraction are accomplished simultaneously.

FIG. 7 depicts apparatus 200 deployed over a guidewire, guidewire 242, which can be placed similar to guidewire 42 of FIGS. 2 through 5, such that it passes from the Aorta to the IVC. Guidewire 242 is shown passing through arterial wall 231, such as the wall of the Aorta, and venous wall 221, such as the wall of the IVC. Outer sheath 212 is shown passing through both arterial wall 231 and venous wall 221 to assist in the deployment of clip 250. In order to cross through the vessel walls, apparatus 200 may include a flow path enlarging element such as an integrated balloon element and/or apparatus 200 may include a dilating slope on one or more distal ends. Apparatus 200 of FIG. 7 depicts clip 250 being placed from artery to vein, however it should be appreciated that a vein to artery placement can be similarly accomplished by apparatus 200 and would result in a similarly placed clip 250.

In FIG. 7, clip 250 is partially deployed, to partially deploy the self-expanding distal end 251 of clip 250. Deployment is initiated such as by advancing core 211 while maintaining outer sheath 212 in a fixed position, by retracting sheath 212 while maintaining core 211 in a fixed position, or by both, perhaps simultaneously, advancing core 211 and retracting sheath 212. Proximal end 252 of clip 250 remains constrained by outer sheath 212. During the deployment process, apparatus 200 or any portion of apparatus 200 can be retracted while injecting contrast medium. Contrast medium can be injected through apparatus 200, or through a venous catheter or separate arterial catheter. Contact of the distal flange of clip 250 can be confirmed by visualizing bulging of either or both the venous wall 221 and the arterial wall 231 during a contrast medium injection.

In FIG. 8, clip 250 has been further deployed, and outer sheath 212 retracted to expose venous wall 221 and arterial wall 231. In an alternative embodiment, outer sheath 212 does not pass through arterial Wall 231 and/or venous wall 221 and clip 250 is pushed through both walls during deployment.

FIG. 9 depicts a fully deployed clip 250, providing an anastomotic connection between arterial wall 231 and venous wall 221 such as to provide a flow path, or fistula between an artery and vein such as the Aorta and IVC. Clip 250 can provide numerous functions as has been described hereabove including but not limited to prevention of blood leakage outside the two vessels, maintenance of the flow path between the two vessels, and other functions. In FIG. 9, guidewire 242 has been removed and the procedure can be considered complete. In a preferred embodiment, guidewire 242 remains in place, and subsequent operations can be performed to enhance the outcomes and/or therapeutic benefits of the procedure, or to complete one or more other interventional procedures such as those performed in either the starting vessel, or target vessel by way of the starting vessel.

During retraction of apparatus 200 or one of its components, a balloon integrated on the core 211 of apparatus 200, not shown, may be inflated to help bias clip 250 in an open position during retraction. This particular embodiment may also be important if retro-peritoneal bleeding is suspected. Prior to complete retraction, a contrast medium injection from the arterial side can be used to assess blood flow through the fistula. In a preferred embodiment, guidewire 240 is not removed until proper flow and/or sufficient therapeutic benefit are confirmed. If flow is determined to be insufficient, or even too great, subsequent procedures can be employed to change the flow characteristics, such procedures described in more detail herebelow.

Figure 10:
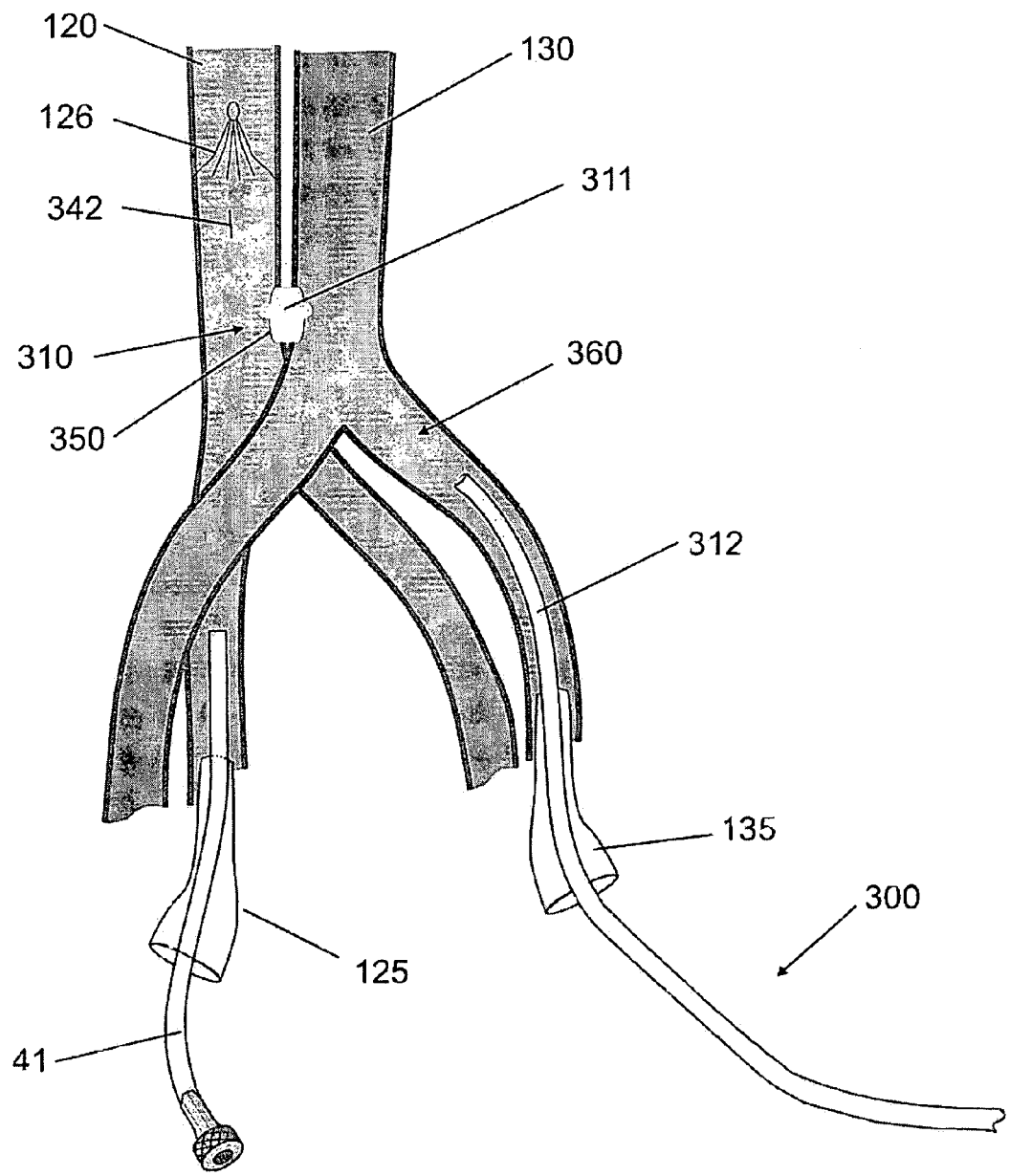
FIG. 10 illustrates a fistula treatment device consistent with the present invention.

FIG. 10 depicts a fistula modification procedure and apparatus such that flow through the fistula can be increased or decreased, or other characteristics of the fistula can be improved or otherwise modified to provide enhanced therapy to the patient. Shown in FIG. 10 is Aorta 130 and IVC 120 after a fistula 310 has been created using one or more techniques described in this application. Clip 350 has been placed between Aorta 130 and IVC 120 to provide and maintain long term flow of highly oxygenated arterial blood into the venous system at a point relatively near the right atrium of the heart. Placed in a right femoral vein is venous introducer 125, and an imaging catheter 41 introduced through venous introducer 125 such that its tip resides at a location proximal to fistula 310. Inserted into the left femoral artery of the patient is arterial introducer 135, and fistula maintenance apparatus 300. Fistula maintenance apparatus 300 is placed over a guidewire, guidewire 342, which passes through fistula 310, from artery to vein, similar to the wires placed in the fistula creation procedures described hereabove. In a preferred embodiment, guidewire 342 was the guidewire used to create fistula 310, and has remained in place since originally placed from Aorta 130 to IVC 120. Alternatively, guidewire 342 can be placed using standard interventional guidewire techniques after fistula 310 has been created. A pigtail catheter or other contrast medium injection catheter, not shown, may be place via the Right or Left Iliac Arteries, such that its tip is superior to fistula 310, to visualize fistula flow with contrast medium injections.

Apparatus 300 includes outer sheath 312 which slidingly receives one or more internal components within one or more internal lumens. Fistula treatment device 360 is a catheter device including an inner surrounding guidewire 342 such that as either fistula treatment device 360 or apparatus 300 are advanced, the advancement tracks along guidewire 342. Fistula treatment device 360 includes near its distal end, fistula treatment element 311 which has been advanced to remain within the inner diameter of clip 350 of fistula 310. Fistula treatment element 311 can take numerous forms to increase or decrease the flow through fistula 310, modify the structure of clip 350 or fistula 310, add or remove material or agents from fistula 310 or clip 350, or otherwise modify one or more characteristics or properties of clip 350 or fistula 310.

In a preferred embodiment, fistula treatment element 311 is a balloon used to dilate clip 350 and fistula 310. Clip 350 may be constructed of plastically deformable materials, either totally or partially, such that dilation will expand those materials to a greater diameter. For example, clip 350 may include self-expanding material at its ends, and plastically deformable materials at its midsection that that dilation increased the diameter of the midsection and resultant fluid pathway at one or more locations along the fistula. Dilation of a fully self-expanding clip 350 may also be appropriate to allow further expansion of clip 350 due to expansion and/or deformation of the tissue surrounding clip 350. Decrease in fistula flow can be accomplished by decreasing the diameter at one or more locations along the fistula, such as with a specialized device that pulls a portion of the midsection of clip 350 towards a smaller diameter.

In another preferred embodiment, fistula treatment element 311 may include deployment of a second implant, not shown, to increase or decrease flow properties, to provide one or more drugs or agents, or to otherwise modify the fistula and/or clip 350. Placement of a second implant may be used to enhance scaffolding, prevent bleeding, reduce lumen diameter and/or perform another function.

In another preferred embodiment, fistula treatment element 311 may include an element to perform one or more of the following functions: covering a portion of the anastomotic clip, applying an antibiotic agent, applying an anti-infective agent; applying an anti-proliferative agent, applying a source of light, applying a source of heat, applying a source of cooling, applying an anti-thrombotic agent and/or providing a dose of radiation.

Modification of fistula 310 may be performed during the same procedure that created fistula 310, such as within an hour of the creation of fistula 310 and over the same guidewire used to deploy clip 350, or the modification procedure can be performed in a subsequent procedure such as a procedure greater than twenty four hours from the creation of fistula 310. In such a subsequent procedure, a new guidewire, introduced from either Aorta 120 or IVC 130 can be manipulated using standard interventional techniques, to access the fistula and cross over to the connected vessel, either in the same direction as used in fistula creation or the opposite. Apparatus 300 can then be advanced over the vessel to vessel guidewire to perform the fistula modification or treatment procedure.

Also depicted in FIG. 10 is vena cava filter 126, placed in IVC 120 at a location between fistula 310 and the right atrium of the heart. It may be advantageous for filter 126 to be in place during part or the entire fistula creation procedure to prevent blood clots that may be creating during fistula creation from reaching the pulmonary circulation. In addition, vena cava filter 126 may remain implanted after the completion of the procedure, for the duration of therapy or longer. Other filter devices, not shown, such as umbrella and other devices including those used in saphenous vein graft atherectomy procedures, may be placed in either the venous or arterial flow, or both, to prevent and potentially remove undesired embolus caused by or created during the fistula creation procedure.

Additional and/or alternative flow modification procedures can be performed to increase or decrease flow of arterial blood into the venous system. For example, creation of a second fistula between the Aorta 130 and IVC 120, not shown, or other location between an artery and a vein, can be made to increase flow. The second fistula can be created during the same procedure as the first fistula creation procedure, such as within an hour of the first fistula creation, or in a subsequent procedure such as a procedure more than twenty four hours from the creation of the first fistula. The flow modification procedure can be performed before the anastomotic clip is placed, or after it is in position between artery and vein.

In a preferred embodiment, fistula maintenance apparatus 300 of FIG. 19 includes a visualization element such as an ultrasound element, not shown. The visualization element may be an ultrasound catheter, such as a rotational or fixed array ultrasound catheter, which is inserted in a lumen of fistula maintenance apparatus 300, or may be an integrated ultrasound device has as an array of ultrasound crystals which are fixedly mounted along the distal portion of fistula maintenance apparatus 300 and contain electronic connections that are connected to a proximal handle of fistula maintenance apparatus 300 and mate with a standard ultrasonic viewing monitor, all not shown. In an alternative or additional preferred embodiment, fistula maintenance apparatus 300 of FIG. 10 includes one or more visualization markers, such as radiographic markers or embedded agents, or ultrasound markers, all not shown. These markers can be used to perform controlled advancements, retractions, rotations and other positioning of fistula maintenance apparatus 300 during the fistula creation procedure.

Figure 11:
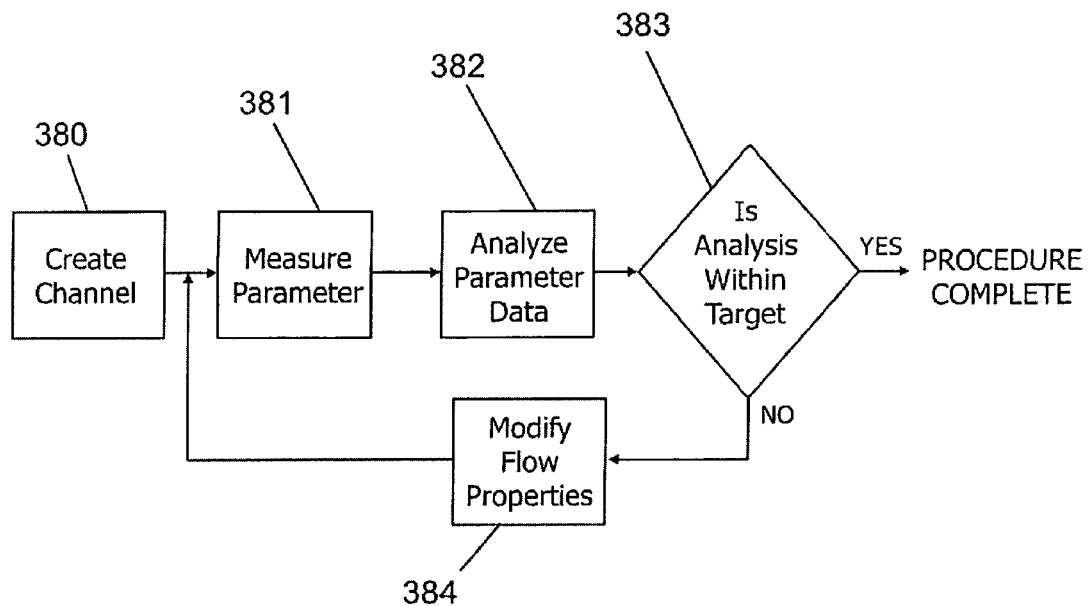
FIG. 11 show a flow diagram of an exemplary method of treating a fistula site to improve therapeutic benefit.

FIG. 11 depicts a methodology of modifying one or more flow properties of the fistula based on the measurement of one or more physiologic parameters. Step 380 includes the creation of the initial fistula wherein oxygenated blood from one or more arteries is provided through an anastomotic connection to one or more veins. After the fistula is created, Step 381 depicts the measurement of one or more physiologic parameters, including but not limited to: blood pressure, heart rate, cardiac output, Pa $O_2$, PaC $O_2$, Pv $O_2$, PVC $O_2$, PApr, PI $O_2$, $O_2$ saturation, mean system arterial pressure, mean system venous pressure, respiration, blood glucose, heart rate variability or other heart parameter. In step 382, an analysis of the data collected in Step 381, such as by the aid of a software embedded device, is performed. In Step 383, the results of the analysis are compared to one or more clinical outcome target values or other types of outcome target values, such that if one or more targets are achieved, the procedure is complete and no flow modification procedures are performed at that time. If one or more target values are not achieved, a flow modification procedure is performed in step 384. While this may be the last step of this assessment procedure, in a preferred embodiment, a repeat parameter measurement is performed, by repeating step 381 as shown in FIG. 1, and subsequent steps 382 and 383, and 384 as appropriate are performed until the output of step 383 indicates target values have been achieved. One or more parameters can be measured and assessed in the method described hereabove. A first parameter may be used for initial assessment, and a different for a subsequent assessment. Physiologic measurements can be assessed individually, or in combination with one or more other physiologic parameters. Outcome target values can be based on a single physiologic measurement and analysis, or a combination of multiple analyses to determine satisfactory flow conditions. The flow modifications can be performed multiple times. Target levels can be adjusted based on patient condition, procedure time or other procedure parameter (e.g. amount of contrast medium used), or amount of flow modifications performed. Other variables and parameters can be integral to or other otherwise impact the analysis of FIG. 11 including but not limited to: patient disease state, first outcome target level, second outcome target level, duration of procedure, number of flow modification procedures performed, outcome of previous analysis of physiologic data, outcome of analysis of different set of physiologic data, patient age or other patient parameter.

In a preferred embodiment, a luminal diameter for the fistula and resultant flow rate is chosen to be at the lower end of a target size and/or flow rate. Subsequent to initial fistula creation, one or more parameters are measured and assessed according to steps 381, 382 and 383. The flow properties are increased, such as via the fistula maintenance apparatus 300 described in relation to FIG. 10, the increase targeted to be a relatively small amount to avoid providing more flow than is needed to reach optimal target levels. The flow modifications are repeated, each time minimizing the flow increase such as to "fine tune" or otherwise reach target levels without surpassing optimum flow conditions.

Figure 12:
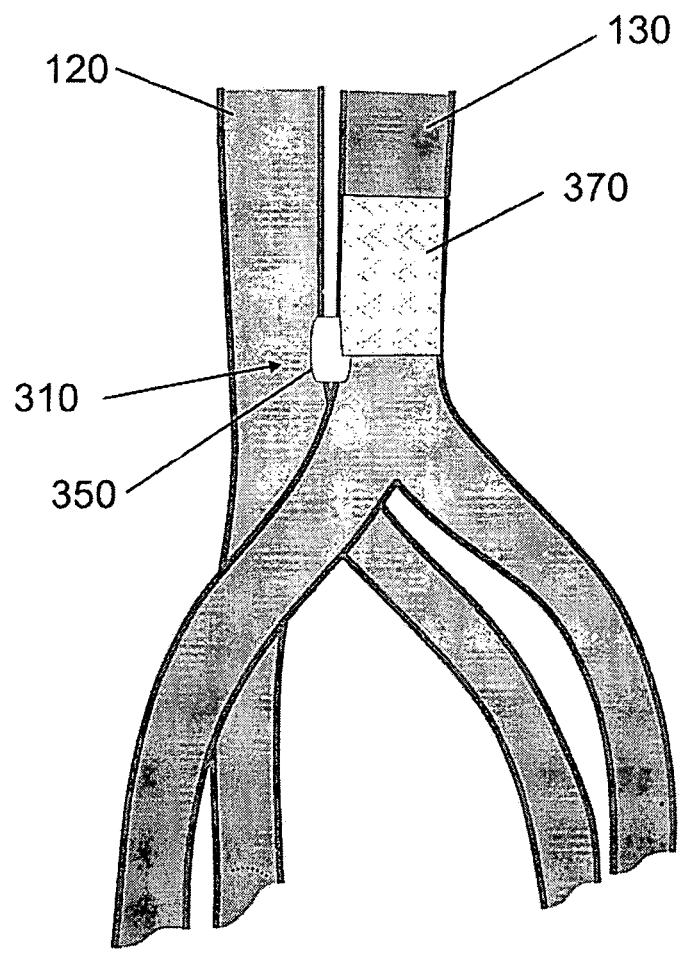
FIG. 12 illustrates a fistula including an anastomotic clip that is partially covered to modify the flow of arterial blood into the venous system.

FIG. 12 depicts an example of a flow modification procedure in which flow through a fistula is decreased. Fistula 310 has been created, such as in a procedure more than twenty four hours prior to the flow modification procedure, between Aorta 130 and IVC 120 and including clip 350. In the subsequent flow modification, requiring only access to the Aorta 139, such as by way of the right femoral artery, a covered stent 370 is placed which partially covers the opening of fistula 310. The placement of covered stent 370 did not require a guidewire to be placed through the fistula 310. Other flow reduction techniques, described hereabove, can be made at the time of fistula creation or during a subsequent procedure.

In an alternative embodiment, covered stent 370 is placed to completely cover clip 350 and fistula 310 ceasing all fistula flow. This cessation of flow may be desirous if certain adverse conditions outweighed the benefit of the fistula flow, if there was insufficient patient improvement, and/or if the need for the fistula flow has subsided. The fistula flow may be indicated to be stopped based on assessment such as an assessment performed in the methodology described in reference to FIG. 11.

Figure 13:
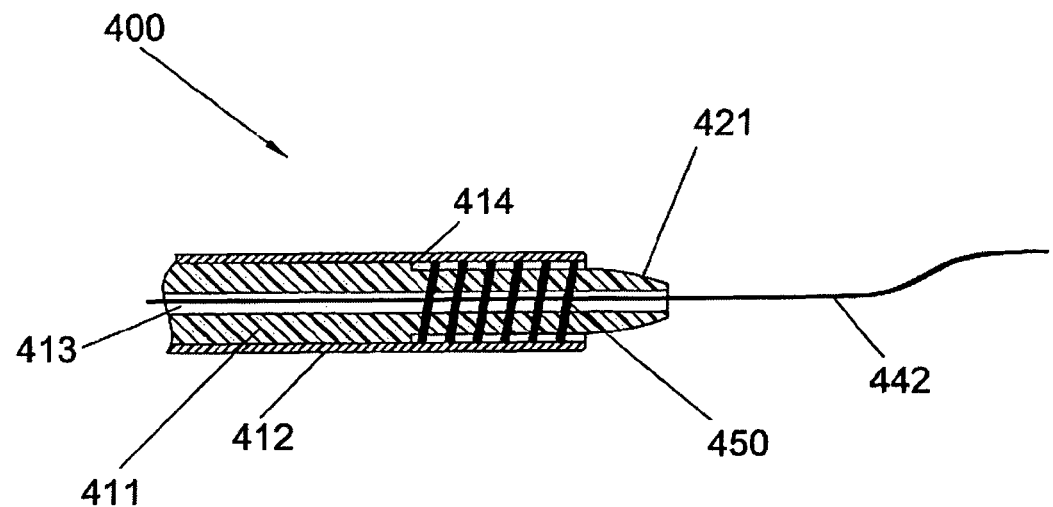
FIG. 13 illustrates a cross sectional view of an apparatus for delivery of an anastomotic clip consistent with the present invention.

Referring now to FIG. 13, apparatus 400, another preferred embodiment of an apparatus for delivering a vessel to vessel anastomotic clip, clip 450 is disclosed. Each of the sliding tubes and activatable elements of apparatus 400 include one or more controls, as do similar apparatus in FIGS. 14 and 15a through 15e, located on the proximal end or handle of apparatus 400, all not shown but similar to the controls shown in reference to apparatus 10 of FIGS. 2 through 5. Apparatus 400 includes a slidable flexible tube, core 411 which includes a guidewire lumen, lumen 413, from its proximal end, not shown, to its distal end, shown with guidewire 442 inserted therethrough. Each of the sliding elements, such as tubes, needles, cores and catheters, can have biasing members located along their pathway such as in a proximal handle, which are elastically biased, such as by way of a spring mechanism, to be biased toward an advanced or retracted position. In a preferred embodiment, the sliding needle element, not shown, is elastically biased to be in a retracted position to avoid an operator repositioning apparatus 400, while the needle is inadvertently in an extended or otherwise exposed condition.

Surrounding core 411 is outer sheath 412, also made of flexible materials such that apparatus 400 can be advanced in its entirety, over a guidewire and through specific vasculature of human and other animal patients. Core 411 includes a reduced diameter, or step, step 414, near its distal end and clip 450 is located at this reduced diameter portion and within the diameter of outer sheath 412 such that if clip 450 is constructed of self-expanding materials, outer sheath 412 will maintain clip 450 in a compressed configuration. If core 411 is advanced, step 414 will provide sufficient force on clip 450 such as to push clip 450 out of outer sheath 412.

Figure 14:
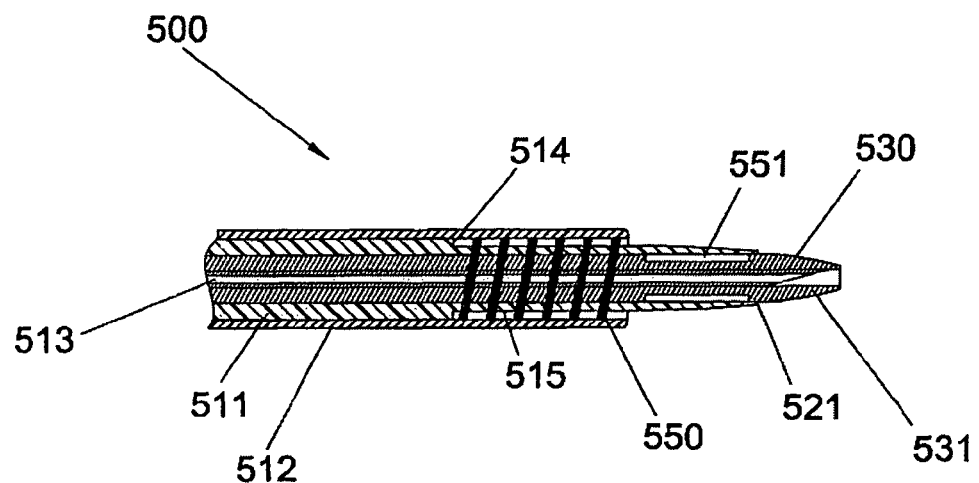
FIG. 14 illustrates a cross sectional view of an apparatus for delivery of an anastomotic clip consistent with the present invention.

Referring now to FIG. 14, apparatus 500, another preferred embodiment of an apparatus for delivery of a vessel to vessel anastomotic clip is disclosed. Apparatus 500 includes an elongate tube, core 511, which includes a guidewire lumen, lumen 513 from its proximal end, not shown, to its distal end. Core 511 has near its distal end, a reduced diameter segment, segment 515, such that a step exists, step 514 just prior to segment 515. Core 512 has a dilating tip, tip 521 at its distal end. Surrounding core 511 is outer sheath 512, in which core 511 is slidingly received. Captured between segment 515 and outer sheath 512 is a vessel to vessel anastomotic clip, clip 550, which may be self-expanding, balloon expandable or both. Not shown is a handle, on the proximal end of apparatus 500 which contains controls to advance and retract the outer sheath 512 and core 511 in order to deploy clip 550 as has been described in various forms hereabove in reference to similar apparatus.

Apparatus 500 of FIG. 14 further includes a flexible tube, needle sheath 531, which is slidingly received within a lumen of core 511 and includes a lumen from its proximal end to its distal end, in which a flexible needle, needle 530, can be slidingly advanced and retracted such that needle 530 can protrude from the distal end of needle sheath 531 to penetrate the wall of one or more vessels. Needle 530 may have a predetermined shape or trajectory, which when confined within one or more lumens of apparatus 500 is overcome to take on the shape of apparatus 500. However, when advanced from the tip of needle sheath 531, the predetermined shape or trajectory of needle 530 is utilized to facilitate puncturing out of the "starting" vessel in which distal portion of apparatus 500 is placed, and into a "target" vessel which is preferably in close proximity to the starting vessel. Typical unconfined needle shapes may be straight, curved, such as a curve of less than thirty degrees, and may include multiple bends.

The apparatus 500 of FIG. 14 further includes means of modifying a fistula and/or clip 500 after it is placed in the fistula. Included is fistula treatment element 551, used to modify flow or other property of the fistula, which may be one or more of: a compliant or non-compliant balloon, such as to expand clip 550; a heating or cooling element or site; a radiation element or site; a drug and/or agent delivery element or site; a light emitting element or site such as to activate a photo-active drug or agent; or other fistula modifying element. Apparatus 500 may include one or more radiographic or ultrasound markers, such as to located the anastomotic clip 550, step 514, one or more device tips, or other specific device locations useful in the creation of a flow path between an artery and a vein and placement of clip 550 between the artery and vein.

Figure 15A:
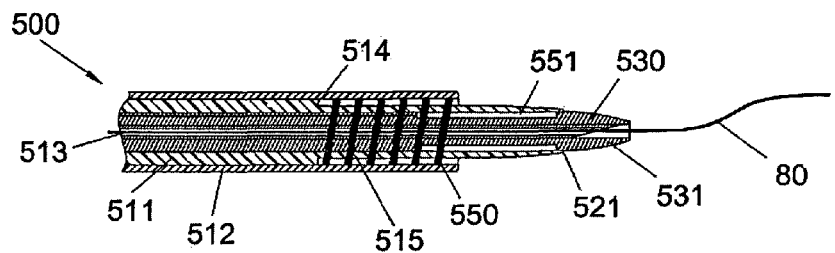
FIGS. 15a through 15e illustrate cross sectional view of an apparatus for delivery of an anastomotic clip consistent with the present invention.

Depicted in FIGS. 15a through 15e is the apparatus 500 of FIG. 14 shown in various stages of fistula creation and anastomotic clip deployment. The specific vessels including vessel walls have been omitted for drawing simplification, noting that detailed descriptions of the procedure have been provided hereabove. In FIG. 15a, apparatus 500 is advanced over a standard interventional guidewire, guidewire 80 to a location proximate the eventual fistula site, in a starting vessel, either an artery or a vein. After reaching the fistula site, guidewire 80 is removed. Needle sheath 531 has needle 530 retracted, such as may be automatically performed by a spring-loaded retraction mechanism, not shown. The tip of needle sheath 531 is manipulated toward the vessel wall intended to be the site of the fistula.

Figure 15B:
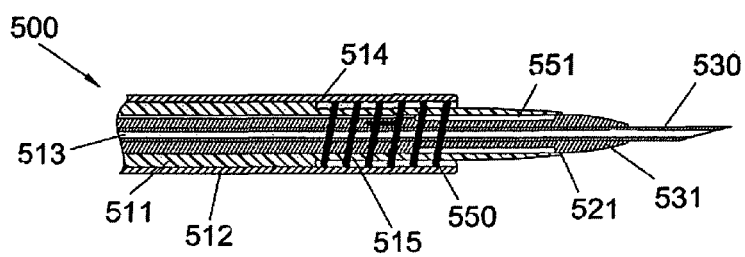
Figure 15C:
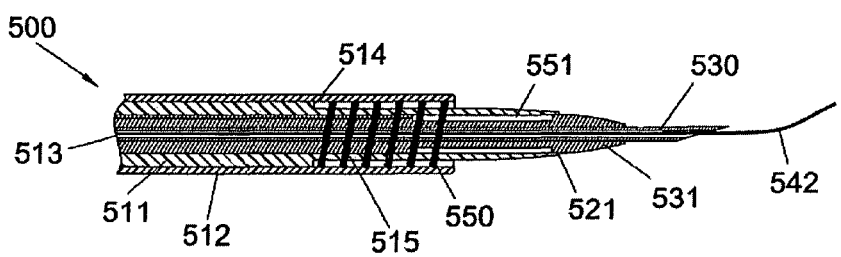

Referring now to FIG. 15b, while the tip of needle sheath 531 is at the intended fistula crossing location, needle 530 is advanced utilizing proximal controls of apparatus 500, not shown. Various techniques, described in detail hereabove, can be used prior to, during and after needle advancement to confirm proper location of one or more components of apparatus 500 especially the tip of needle 530. Advancement can be in one motion, such as by an automatic injector, not shown, or in discrete steps. Blood can be aspirated to confirm access of the target vessel, and/or contrast medium can be injected to confirm access. In an alternative technique, a guidewire in the lumen of the needle is brought to the tip and is very slowly advanced and/or or slight forward force is intermittently or continuously applied, such that when the needle passes into the target vessel, the guidewire will advance down the lumen of the target vessel. FIG. 15c shown guidewire 542 advanced out of the lumen of needle 531.

Numerous alternatives prior to deploying anastomotic clip 550 can be employed to simplify delivery. One or more luminal tubes, such as needle sheath 531 and needle 530, can be removed or partially retracted. In alternative embodiments, one or more of these luminal tubes may include dilating tips to assist in these tubes crossing through the starting vessel and target vessel walls. One passed through, a dilating or other enlarging element incorporated into one or more of these advanceable tubes can be used to create a fluid flow channel or flow path between the vessels.

Figure 15D:
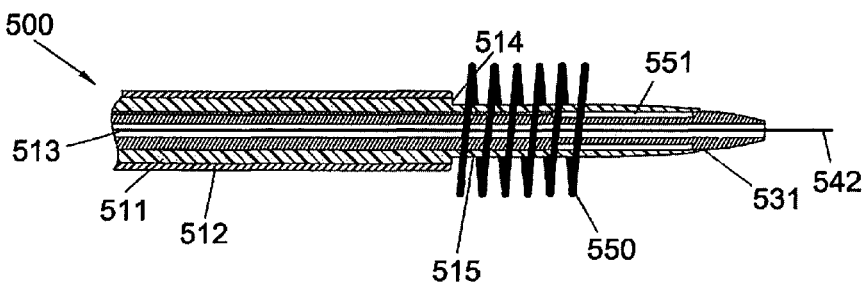

Referring now to FIG. 15d, needle 530 has been retracted and removed leaving needle sheath 530 and guidewire 542 in place. Needle sheath 530 has a dilating tip to assist in crossing from vessel to vessel such that reduced diameter segment 515 and clip 550 are properly located for delivery of clip 550 into the flow path between the two vessels. In a preferred embodiment, apparatus 500 is advanced such that clip 550 is located a small distance past the fistula creation site, and clip 550 is placed while retracing one or more portions of apparatus 500. Clip 550 in FIG. 15d is shown in its fully expanded position. Various techniques can be employed wherein clip 550 is partially deployed and one or more portions of apparatus 500 are retracted or advanced, such as a retraction procedure to enhance tension between the target vessel and starting vessel walls.

Figure 15E:
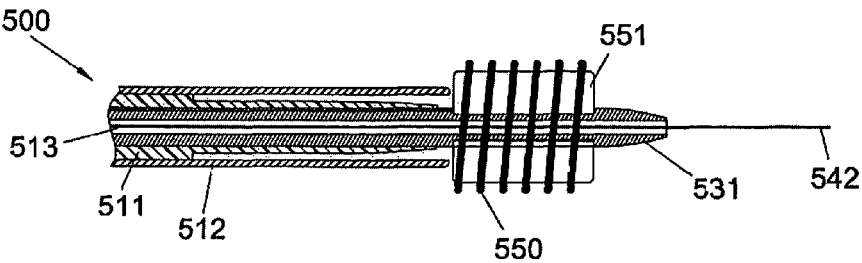

Referring now to FIG. 15e, core 511 has been partially retracted, exposing fistula treatment element 551, and needle sheath 531 has been partially retracted to located fistula treatment element 551 within the length of clip 550. As stated hereabove, fistula treatment element 551 may take on various forms for treating and/or modifying the fistula and/or clip 550. Fistula treatment element 551 of FIG. 15e is a balloon, which acts as a fistula enlarging element and is used to expand the fistula, either by expanding a plastically deformable portion of clip 550 or expanding the tissue surrounding clip 550, not shown, or both. Note that in alternative embodiments, fistula treatment element 551 could be incorporated into one or more portions of apparatus 500, such as core 511, outer sheath 512 or needle sheath 531, or fistula treatment element 551 could be introduced as a separate device, such as a device inserted through one or more lumens of apparatus 500. Alternative fistula enlarging elements include debulking elements, such as radiofrequency ablation devices and rotational cutting elements.

In a preferred embodiment, apparatus 500 of FIGS. 15a through 15e includes a visualization element such as an ultrasound element, not shown. The visualization element may be an ultrasound catheter, such as a rotational or fixed array ultrasound catheter, which is inserted in a lumen of apparatus 500 and can be removed from apparatus 500 during advancement, retraction or other step of the fistula creation procedure. Alternatively, the visualization element may be an integrated ultrasound device that has as an array of ultrasound crystals which are fixedly mounted along the distal portion of apparatus 500 and are attached to electronic connections that are connected to a proximal handle of apparatus 500 and mate with a standard ultrasonic viewing monitor. In an alternative, preferred embodiment, apparatus 500 of FIGS. 15a through 15e includes one or more visualization markers, such as radiographic markers or embedded agents, or ultrasound markers, all not shown. These markers can be used to perform controlled advancements, retractions, rotations and other positioning of apparatus 500 during the fistula creation procedure such as by positioning relative to anatomical landmarks including bifurcations, vessel walls, etc. These markers can be integrated into one or more of: the outer sheath 512, core 511, a vessel crossing needle catheter and a balloon catheter.

Figure 16:
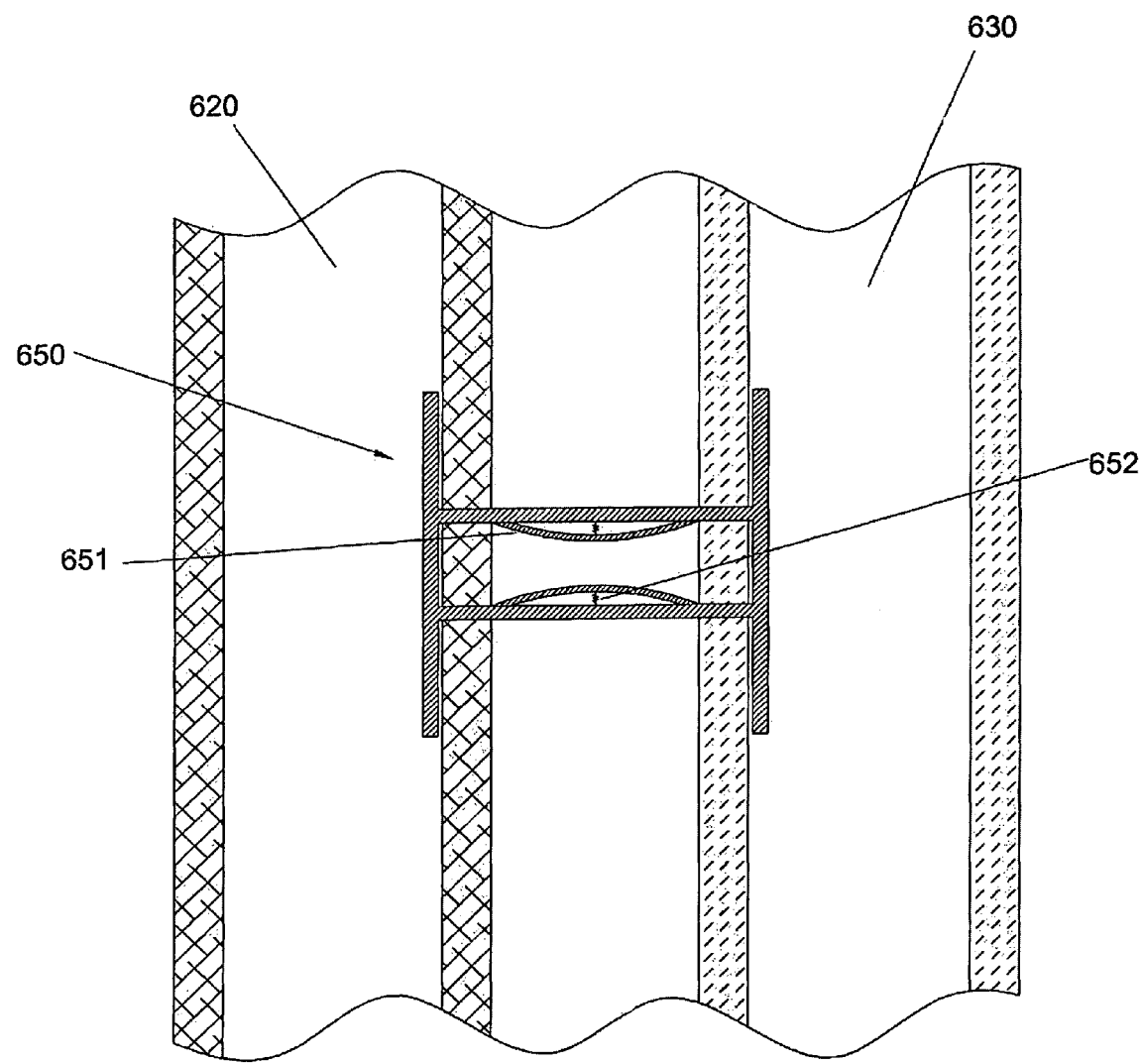
FIG. 16 illustrates an anastomotic clip deployed in a fistula consistent with the present invention.

Referring now to FIG. 16, a preferred embodiment of an anastomotic clip is shown wherein an automatic flow adjustment element is integral to clip 650. Clip 650 is shown in an implanted configuration, such as between artery 630 and vein 620. Clip 650 can provide one or more functions such as scaffolding the tissue between the fistula vessels, providing tension between the walls of the two fistula vessels such as to prevent bleeding, acting as a drug or agent depot for prolonged delivery to the fistula site or providing one or more other functions intended to improve flow characteristics or long term patency of the fistula, or provide some other therapeutic benefit to the patient. Clip 650 of FIG. 16 includes a flow control element that can automatically adjust the flow characteristics of the fistula based on one or more physiologic parameters. Clip 650 includes along its inner diameter a covering, covering 651, constructed of super elastic metal, such as a form of nickel titanium alloy, or other biocompatible material such as polytetrafluoroethylene. Covering 651 is biased in a bowed configuration by one or more springs such as spring 652, such bias creating a reduced minimal internal diameter of the flow path of clip 650. Blood will flow from the higher pressure arterial system to the venous system through the internal lumen of clip 650. Based on the pressure applied at the covering, the springs will adjust accordingly to a certain diameter profile along the lumen of clip 650. As arterial pressure increases, the applied covering pressure will also increase, causing one or more springs 652 to compress, thus allowing the covering to expand outwardly increasing the average luminal diameter along clip 650. This increase in average luminal diameter will result in more flow from artery to vein, through clip 650, as arterial pressure increases.

The clip 650 of FIG. 16, as well as the other embodiments of anastomotic clips of the present invention, can be constructed of various materials including various biocompatible metals, such as stainless steel, titanium and nickel titanium alloy, as well as one or more biocompatible polymers. Materials can be selected such that clip 650 self-expands or can be expanded by a dilating device such as a balloon. Alternatively, clip 650 may include sections of different material construction, such that a first portion is self expanding and a second portion is plastically deformable. Clip 650 may include in its construction a temperature activated shape memory alloy, which changes shape at body temperature or at another temperature controllable by a clinician, such as to adjust flow or other characteristics.

Clip 650 may consist of a single component or multiple components. In multiple component configurations, all the components may be configured to be implanted in a single deployment or multiple deployments. After deployment, it may be desirable to remove one or more components of clip 650 at a time such as within an hour of original placement, or at a time more than twenty four hours from initial placement.

Anastomotic clip 650 may include a covering along its entirety, or include a covering limited to one or more portions along its length or diameter. Coverings may consist of a single substance, or multiple types of coverings can be used at different locations along the periphery of clip 650. Covering materials may include one or more of polytetrafluoroethylene, elastomer, nickel titanium alloy or other biocompatible material. Coverings may be porous or impermeable, and may be biodegradable. Clip 650 covering and/or other materials of construction may include or be coated with one or more agents to prevent atheroma or infection, such agents described in detail hereabove. An alternative approach to long term patency would be to have a roughened or sintered surface on the inner diameter of clip 650, in an attempt to cause clot to occur without losing fluid flow, the clot itself evolving through a healing process to the eventual creation of an endothelial layer along the inner diameter of clip 650.

Different geometric configurations of clip 650 can be utilized to maintain the arterio-venous fistula. In a preferred embodiment, geometries and materials of construction are chosen such that the radial force exerted at the mid-section is greater than the radial force exerted at either or both ends. In another preferred embodiment, the diameter of clip 650 is larger at one or both ends than at the midsection. In another preferred embodiment, the length of clip 650 when expanded is less than or equal to the largest diameter of the inner lumen. In another preferred embodiment, the length of clip 650 when expanded is less than the length when it is compressed and maintained within an other sheath. In another preferred embodiment, one or more ends of clip 650 are trumpet shaped. In another preferred embodiment, clip 650 is designed to have minimal contact with artery and/or vein intima. In another preferred embodiment, one or more ends of clip 650 traverses more than ninety degrees from its central axis to form a doughnut or toroid shape. Note that this particular embodiment accommodates greater distance between vessel walls, and requires less precision in placement.

In another embodiment, clip 650 has an inner lumen between one and fifteen millimeters when expanded, and in a preferred embodiment the inner lumen is between two and ten millimeters when expanded. In another embodiment, clip 650 has an integrated sensor, not shown, that can be used to measure flow control or flow information, such as through the use of imaging or via embedded electronics wirelessly transmitted to an outside receiver.

It is important that anastomotic clip 650 not migrate after it is placed between artery 630 and vein 620. In order to maintain a secure placement, fixation means can be used, not shown, including but not limited to one or more of: suture, staples, clips and biocompatible glues.

Figure 17:
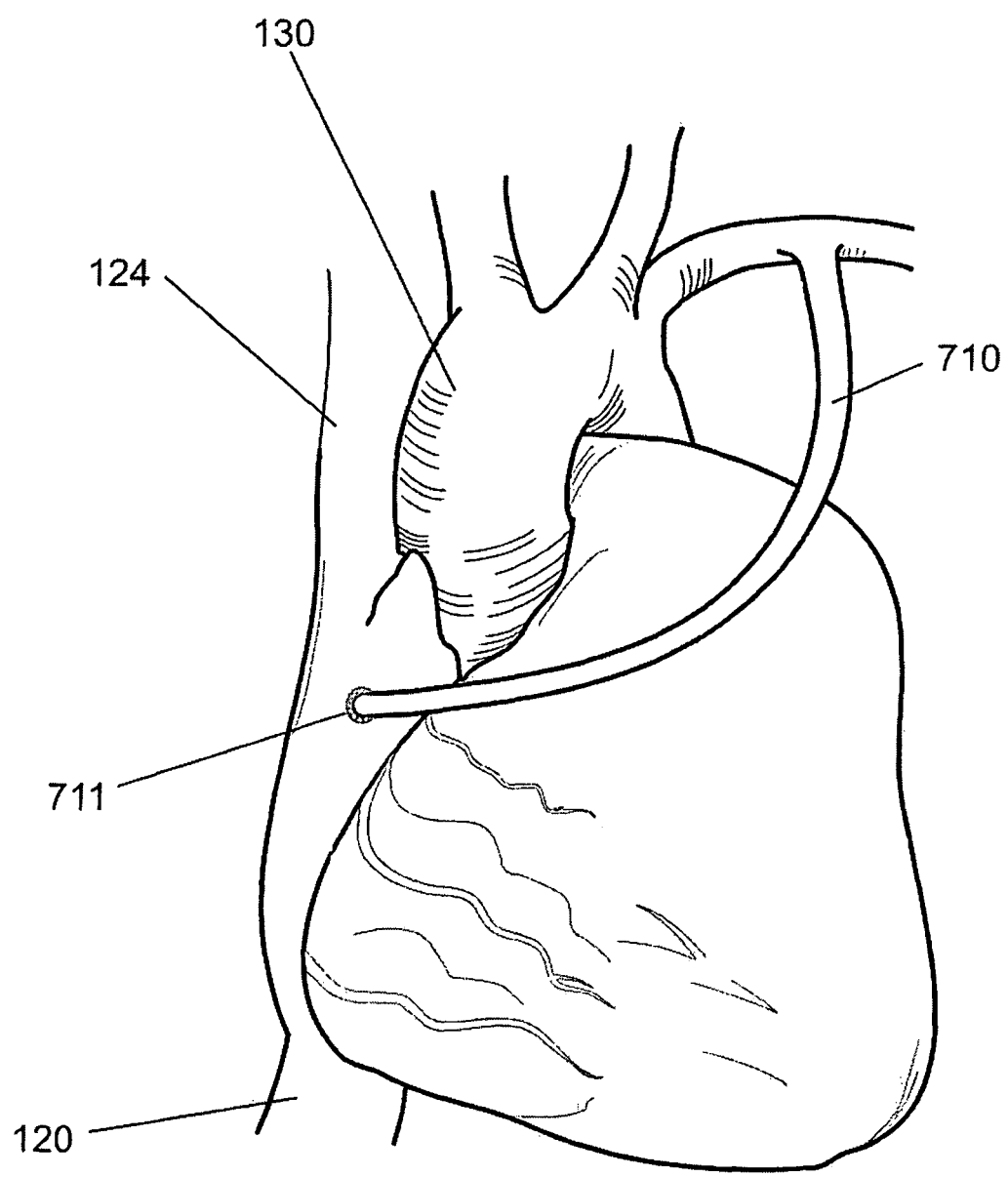
FIG. 17 illustrates a Left Internal Mammary Artery connected with an end to side anastomosis to the Vena Cava at a location proximate the Right Atrium of the heart.

Referring now to FIG. 17, a method of providing oxygenated blood to the venous circulation of a patient is described wherein a non-cardiac vein is attached to one end of a flow conduit, the flow conduit attached at its other end to a source of arterial blood. Depicted in FIG. 17 are Aorta 130, Inferior Vena Cava IVC 120, and Superior Vena Cava SVC 124. The Left Internal Mammary Artery, or LIMA 710, has been freed from the inside of the breast, and attached with an end to side anastomosis 711 to the Vena Cava near the Right Atrium of the heart. The Left Internal Mammary Artery 710 acts as a flow conduit to provide oxygenated blood to the venous system such that blood flowing into the lungs is at a higher oxygen content than before the arterial flow conduit was attached. Therapeutic benefit can be achieved from the decrease in systemic vascular resistance that occurs, as well as from the raise in the percentage of oxygen in the venous blood entering the lungs. These therapeutic benefits are applicable to patients afflicted with one or more of: chronic obstructive pulmonary disease, congestive heart failure, hypertension, hypotension, respiratory failure, pulmonary arterial hypertension, lung fibrosis and adult respiratory distress syndrome.

Anastomosis 711 of FIG. 17 can be created by one or more surgical procedures including an open surgical procedure and various minimally invasive procedures such as laparoscopic procedures, small opening beating heart procedures, and other less invasive surgical procedures. Alternatively, a percutaneous approach or interventional procedure may be used with specialized devices used to exit vessels in a controlled manner. Anastomosis 711 may be accomplished with standard anastomotic end to side suturing techniques and/or with the assistance of a mechanical anastomotic clip.

Various cardiac veins, or vein locations can be used in the method of FIG. 17 such as the Vena Cava, Superior Vena Cava, Inferior Vena Cava, Common Iliac Veins or other veins in relatively close proximity to the right atrium of the heart and the pulmonary circulation. Various flow conduits can be used, both natural and artificial, such as Left Internal Mammary Artery (LIMA), Right Internal Mammary Artery (RIMA), a harvested vessel such as a saphenous vein graft or radial artery, and an artificial graft conduit. These flow conduits can be attached to one or more sources of arterial blood, either naturally (no connection surgery or intervention needed) as with the LIMA and RIMA, or by anastomotic or other connection via surgical or percutaneous means. Sources of arterial blood can include the Aorta or other large arteries, or a chamber of the left heart such as the left ventricle.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for delivering an anastomotic clip between an artery and a vein, said apparatus comprising:
   an elongate core with a lumen extending from a proximal end to a distal end, said core including a reduced diameter segment near its distal end, said segment having a shoulder at its proximal end;
   a needle slidably disposed within the lumen of the core and having a sharpened distal tip and a guidewire lumen therethrough;
   an outer sheath which slidingly surrounds the core;
   a self-expanding anastomotic clip configured for placement between an arterial wall side opening and a venous wall side opening so as to provide tension at the site of an anastomotic connection therebetween such that the anastomotic clip holds an outer wall of the artery and an outer wall of the vein surrounding the anastomotic connection closely against one another to create a fluid seal therebetween, said anastomotic clip having a compressed state and an expanded state when delivered; and
   a handle to advance the needle from the core and to retract the sheath over the core to deploy the anastomotic clip between the artery and the vein;
   wherein the core has a dilating tip so that it can be advanced through a penetration through the walls of the artery and vein made by the needle and the anastomotic clip is maintained in the compressed state between the outer sheath and the reduced diameter segment of the core, such that the clip is held axially in place by the shoulder as the sheath is withdrawn proximally over the clip.

2. The apparatus of claim 1 wherein the core has one or more radiopaque markers.

3. The apparatus of claim 2 wherein the radiopaque markers are aligned with the reduced diameter segment of the core.

4. The apparatus of claim 1 wherein the anastomotic clip is composed of nickel titanium alloy, stainless steel, titanium, or a combination of alloy thereof.

5. The apparatus of claim 1 wherein the apparatus comprises a balloon and the anastomotic clip is balloon expandable.

6. The apparatus of claim 5 wherein a balloon is integrated into the reduced diameter segment.

7. The apparatus of claim 1 wherein the anastomotic clip is shape modified by a thermal process.

8. The apparatus of claim 1 wherein the anastomotic clip includes a first portion which includes self expanding materials and a second portion which includes plastically deformation materials.

9. The apparatus of claim 8 wherein the first portion is located at or near a first end of the anastomotic clip and the second portion is located at or near the midsection of said clip.

10. The apparatus of claim 9 wherein the second end of said clip is constructed of self expanding materials.

11. The apparatus of claim 8 wherein after the anastomotic clip is adapted to exert a greater force at the midsection than at one or more end sections.

12. The apparatus of claim 1 wherein after placement, the end portions of the anastomotic clip are larger than the midsection of said clip.

13. The apparatus of claim 1 wherein the anastomotic clip is adapted to have minimal contact with vessel intima after placement.

14. The apparatus of claim 1 wherein the anastomotic clip is adapted to have a length which is less than or equal to its maximum diameter after placement.

15. The apparatus of claim 1 wherein the anastomotic clip is adapted to have a length less than that of the anastomotic clip after placement than when constrained by the outer sheath.

16. The apparatus of claim 1 wherein the anastomotic clip is adapted to have one or more ends with a trumpet shape after placement.

17. The apparatus of claim 1 wherein the anastomotic clip is adapted to have one or more ends of with a doughnut or toroid shape after placement.

18. The apparatus of claim 1 wherein the anastomotic clip inner lumen is greater than or equal to one millimeter and less than or equal to 15 millimeters after placement.

19. The apparatus of claim 18 wherein the anastomotic clip inner lumen is greater than or equal to two millimeters and less than or equal to ten millimeters after placement.

20. The apparatus of claim 1 wherein the anastomotic clip is covered at a portion along its midsection.

21. The apparatus of claim 20 wherein the covering is biodegradable.

22. The apparatus of claim 20 wherein the cover includes one or more of polytetrafluoroethylene and nickel titanium alloy.

23. The apparatus of claim 20 wherein the cover includes at least one of an antibiotic, an anti-infective, an anti-proliferative, and an anti-thrombotic agent.

24. The apparatus of claim 20 wherein the covering includes a roughened inner surface to promote clot formation.

25. The apparatus of claim 1 wherein the anastomotic clip is secured with one or more of sutures, staples and biocompatible glues.

26. The apparatus of claim 1 wherein a portion of the anastomotic clip is removable after placement.

27. The apparatus of claim 1 wherein the anastomotic clip consists of two separate components.

28. The apparatus of claim 27 wherein the two separate components are deployable simultaneously.

29. The apparatus of claim 27 wherein the two separate components are separately deployable.

30. The apparatus of claim 1 wherein the anastomotic clip applies a greater radial force at its midsection than near either end.

31. The apparatus of claim 30 wherein the anastomotic clip is constructed of self-expanding materials.

32. The apparatus of claim 1 wherein the core is adapted to advance the anastomotic clip forward.

33. The apparatus of claim 1 wherein the anastomotic clip is adapted to provide radial force on the tissue it contacts at its midsection.

34. The apparatus of claim 1 wherein the anastomotic clip is adapted to provide radial force on the tissue it contacts at its midsection to maintain a lumen of the anastomotic connection between said artery and said vein.

35. The apparatus of claim 1 wherein the anastomotic clip includes a flow control element.

36. The apparatus of claim 35 wherein the flow resistance through the anastomotic clip decreases when the pressure differential across said anastomotic clip increases.

37. The apparatus of claim 36 wherein at least a portion of the inner diameter of the anastomotic clip increases when said pressure differential increases.

38. The apparatus of claim 36 wherein a portion of the anastomotic clip is elastic.

39. The apparatus of claim 1 wherein the anastomotic clip includes an integrated sensor.

40. The apparatus of claim 39 wherein the integrated sensor provides flow control information.

41. The apparatus of claim 1 further comprising a crossing needle which is slidingly advanceable and has a lumen therethrough.

42. The apparatus of claim 41 wherein the needle is advanced by a needle injection mechanism on the handle.

43. The apparatus of claim 42 wherein the needle injection mechanism is integrated into the handle.

44. The apparatus of claim 41 wherein the vessel crossing needle element is introduced through the core lumen.

45. The apparatus of claim 41 wherein the vessel crossing needle element can be removed from the apparatus.

46. The apparatus of claim 41 wherein the needle is elastically biased in a refracted configuration.

47. The apparatus of claim 41 wherein the needle is curved at its distal end.

48. The apparatus of claim 47 wherein the arc of curvature is less than thirty degrees.

49. The apparatus of claim 47 wherein the needle is straight at its distal end.

50. The apparatus of claim 41 wherein the vessel crossing needle element comprises an integrated visualization element.

51. The apparatus of claim 50 wherein the integrated visualization element comprises an ultrasound imaging device.

52. The apparatus of claim 1 further comprising a fistula enlarging element.

53. The apparatus of claim 52 wherein the fistula enlarging element comprises a balloon.

54. The apparatus of claim 52 wherein the fistula enlarging element includes a tissue debulking device.

55. The apparatus of claim 54 wherein the tissue debulking device comprises a radiofrequency energy delivery element.

56. The apparatus of claim 54 wherein the tissue debulking device comprises a tissue cutting element.

57. The apparatus of claim 52 wherein the fistula enlarging element is integrated into a vessel crossing needle device.

58. The apparatus of claim 52 wherein the fistula enlarging element is integrated into the core.

59. The apparatus of claim 52 wherein the fistula enlarging element further comprises an integrated visualization element.

60. The apparatus of claim 59 wherein said integrated visualization element includes one or more of a radiographic marker, an ultrasonic marker and an ultrasound crystal.

61. The apparatus of claim 52 wherein the fistula enlarging element is utilized more than twenty four hours after the creation of the first fistula.

62. The apparatus of claim 52 wherein the fistula enlarging element is utilized within one hour of the creation of the first fistula.

63. The apparatus of claim 1 further comprising a fistula maintenance device.

64. The apparatus of claim 63 wherein the fistula maintenance device comprises one or more of: a balloon, a debulking device, a radiation source, an implant placement device, an implant removal device, a heating or cooling element, a light emitting element and a drug delivery element.

65. The apparatus of claim 63 wherein the fistula maintenance device comprises a vessel crossing needle device.

66. The apparatus of claim 63 wherein the fistula maintenance device comprises the core.

67. The apparatus of claim 63 wherein the fistula maintenance device further comprises an integrated visualization element.

68. The apparatus of claim 67 wherein said integrated visualization element includes one or more of a radiographic marker, an ultrasonic marker and an ultrasound crystal.

69. The apparatus of claim 1 further comprising one or more visualization markers.

70. The apparatus of claim 69 wherein said one or more visualization markers are positioned to indicate the rotational orientation of the apparatus.

71. The apparatus of claim 69 wherein said one or more visualization markers consist of one or more of: radiopaque markers and ultrasonic markers.

72. The apparatus of claim 69 wherein said one or more visualization markers are alignable with one or more of arterial vessel wall, venous vessel wall and tissue between the artery and vein.

73. The apparatus of claim 69 wherein said one or more visualization markers are integrated into one or more of: the core, the outer sheath, a needle deployment catheter and a balloon catheter.

74. The apparatus of claim 1 further comprising a visualization device.

75. The apparatus of claim 74 wherein said visualization device is an ultrasound device.

76. The apparatus of claim 75 wherein the ultrasound device includes a spinning ultrasound crystal.

77. The apparatus of claim 75 wherein the ultrasound device includes one or more fixed ultrasound crystals.

78. The apparatus of claim 75 wherein the visualization device is slidingly removable from the apparatus.

79. The apparatus of claim 75 wherein the visualization device is integrated into one or more of the core and the outer sheath.

* * * * *

UNITED STATES PATENT AND TRADEMARK OFFICE
CERTIFICATE OF CORRECTION

| | | |
|---|---|---|
| PATENT NO. | : 8,641,747 B2 | Page 1 of 1 |
| APPLICATION NO. | : 11/152621 | |
| DATED | : February 4, 2014 | |
| INVENTOR(S) | : Brenneman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2097 days.

Signed and Sealed this
Eleventh Day of August, 2015

Michelle K. Lee
*Director of the United States Patent and Trademark Office*